(12) United States Patent
Legnini et al.

(10) Patent No.: US 12,286,670 B2
(45) Date of Patent: Apr. 29, 2025

(54) FULL-LENGTH RNA SEQUENCING

(71) Applicant: MAX-DELBRÜCK-CENTRUM FÜR MOLEKULARE MEDIZIN IN DER HELMHOLTZ-GEMEINSCHAFT, Berlin (DE)

(72) Inventors: Ivano Legnini, Berlin (DE); Jonathan Alles, Berlin (DE); Nikolaos Karaiskos, Berlin (DE); Salah Ayoub, Berlin (DE); Nikolaus Rajewsky, Berlin (DE)

(73) Assignee: MAX-DELBRÜCK-CENTRUM FÜR MOLEKULARE MEDIZIN IN DER, Helmholtz-Gemeinschaft Berlin (DE)

( * ) Notice: Subject to any disclaimer, the term of this patent is extended or adjusted under 35 U.S.C. 154(b) by 1063 days.

(21) Appl. No.: 17/281,269

(22) PCT Filed: Aug. 13, 2019

(86) PCT No.: PCT/EP2019/071726
§ 371 (c)(1),
(2) Date: Mar. 30, 2021

(87) PCT Pub. No.: WO2020/069791
PCT Pub. Date: Apr. 9, 2020

(65) Prior Publication Data
US 2022/0002797 A1    Jan. 6, 2022

(30) Foreign Application Priority Data

Oct. 2, 2018    (EP) .................................... 18198248

(51) Int. Cl.
*C12Q 1/68*    (2018.01)
*C12Q 1/6806*    (2018.01)
*C12Q 1/6869*    (2018.01)

(52) U.S. Cl.
CPC ......... *C12Q 1/6869* (2013.01); *C12Q 1/6806* (2013.01)

(58) Field of Classification Search
CPC .................................................. C12Q 1/6869
See application file for complete search history.

(56) References Cited

U.S. PATENT DOCUMENTS

2011/0059453 A1    3/2011    Chamnongpol et al.
2016/0138012 A1*   5/2016    Wickens ................ C07H 21/02
                                                 506/14

FOREIGN PATENT DOCUMENTS

CN         108103055        6/2018
WO    WO 2015/173402      11/2015

OTHER PUBLICATIONS

Adiconis, X. et al. "Comparative analysis of RNA sequencing methods for degraded or low-input samples" Nature Methods, Jul. 2013, pp. 623-629, vol. 10, No. 7, Online Methods pp. 1-4.

(Continued)

Primary Examiner — Kenneth R Horlick
(74) Attorney, Agent, or Firm — SALIWANCHIK, LLOYD & EISENSCHENK

(57) ABSTRACT

The present disclosure provides a method for analyzing a polyribonucleotide, wherein the polyribonucleotide is an mRNA molecule with a poly(A) tail, said method comprising: (a) obtaining a labeled polyribonucleotide by GI tailing; followed by (b) providing a second molecule comprising a first primer recognition sequence followed by a sequence of C nucleotide residues linked to a sequence of T nucleotide residues; followed by (c) obtaining a complex of said labeled polyribonucleotide and said second molecule; followed by (d) obtaining an extended second molecule by (d1) extending the 3' end of the second molecule by synthesizing a sequence that is complementary to the labeled polyribonucleotide; followed by (d2) extending the 3' end of the (Continued)

second molecule by adding at least 1 to 5 C nucleotide residues, followed by a second primer recognition sequence; said method providing information on entire polyribonucleotides, in particular mRNA isoforms and their respective poly(A) tails.

9 Claims, 5 Drawing Sheets

Specification includes a Sequence Listing.

(56) References Cited

OTHER PUBLICATIONS

An, D. et al. "Isoform Sequencing and State-of-Art Applications for Unravelling Complexity of Plant Transcriptomes" *Genes*, 2018, pp. 1-15, vol. 9, No. 43.

Kapteyn, J. et al. "Incorporation of non-natural nucleotides into template-switching oligonucleotides reduces background and improves cDNA synthesis from very small RNA samples" *BMC Genomics*, 2010, pp. 1-9, vol. 11, No. 413.

Legnini, I. et al. "FLAM-seq: full-length mRNA sequencing reveals principles of poly(A) tail length control" *Nature Methods*, Sep. 2019, pp. 879-886, vol. 16, Methods pp. 1-6.

Picelli, S. et al. "Full-length RNA-seq from single cells using Smart-seq2" *Nature Protocols*, 2014, pp. 171-181, vol. 9, No. 1.

Van Dijk, E. L. et al. "The Third Revolution in Sequencing Technology" *Trends in Genetics*, Sep. 2018, pp. 666-681, vol. 34, No. 9.

Written Opinion in International Application No. PCT/EP2019/071726, Oct. 15, 2019, pp. 1-9.

Byrne, A. et al. "Nanopore long-read RNAseq reveals widespread transcriptional variation among the surface receptors of individual B calls" *Nature Communications*, Jul. 19, 2017, pp. 1-11 and online supplementary information pp. 1-9, vol. 8.

Picelli, S. et al. "Smart-seq2 for sensitive full-length transcriptome profiling in single cells" *Nature Methods*, published online Sep. 22, 2013, pp. 1096-1098 and supplemental pp. 1-2, vol. 10, No. 11.

* cited by examiner

SEQUENCE LISTING

```
<160> NUMBER OF SEQ ID NOS: 9

<210> SEQ ID NO 1
<211> LENGTH: 42
<212> TYPE: DNA
<213> ORGANISM: Artificial Sequence
<220> FEATURE:
<223> OTHER INFORMATION: isoTSO
<220> FEATURE:
<221> NAME/KEY: variation
<222> LOCATION: 1
<223> OTHER INFORMATION: /replace="isomeric c"
<220> FEATURE:
<221> NAME/KEY: variation
<222> LOCATION: 2
<223> OTHER INFORMATION: /replace="isomeric g"
<220> FEATURE:
<221> NAME/KEY: variation
<222> LOCATION: 3
<223> OTHER INFORMATION: /replace="isomeric c"
<220> FEATURE:
<221> NAME/KEY: variation
<222> LOCATION: 40
<223> OTHER INFORMATION: /replace="ribo-g nucleotide"
<220> FEATURE:
<221> NAME/KEY: variation
<222> LOCATION: 41
<223> OTHER INFORMATION: /replace="ribo-g nucleotide"
<220> FEATURE:
<221> NAME/KEY: variation
<222> LOCATION: 42
<223> OTHER INFORMATION: /replace="ribo-g nucleotide"

<400> SEQUENCE: 1
nnnaagcagt ggtatcaacg cagagtggcc attacggccn nn                42

<210> SEQ ID NO 2
<211> LENGTH: 47
<212> TYPE: DNA
<213> ORGANISM: Artificial Sequence
<220> FEATURE:
<223> OTHER INFORMATION: dC 3T RT UMI primer
<220> FEATURE:
<221> NAME/KEY: variation
<222> LOCATION: 26
<223> OTHER INFORMATION: /replace="a,g,c,t"
<220> FEATURE:
<221> NAME/KEY: variation
<222> LOCATION: 27
<223> OTHER INFORMATION: /replace="a,g,c,t"
<220> FEATURE:
<221> NAME/KEY: variation
<222> LOCATION: 28
<223> OTHER INFORMATION: /replace="a,g,c,t"
<220> FEATURE:
```

```
<221> NAME/KEY: variation
<222> LOCATION: 29
<223> OTHER INFORMATION: /replace="a,g,c,t"
<220> FEATURE:
<221> NAME/KEY: variation
<222> LOCATION: 30
<223> OTHER INFORMATION: /replace="a,g,c,t"
<220> FEATURE:
<221> NAME/KEY: variation
<222> LOCATION: 31
<223> OTHER INFORMATION: /replace="a,g,c,t"
<220> FEATURE:
<221> NAME/KEY: variation
<222> LOCATION: 32
<223> OTHER INFORMATION: /replace="a,g,c,t"
<220> FEATURE:
<221> NAME/KEY: variation
<222> LOCATION: 33
<223> OTHER INFORMATION: /replace="a,g,c,t"
<220> FEATURE:
<221> NAME/KEY: variation
<222> LOCATION: 34
<223> OTHER INFORMATION: /replace="a,g,c,t"
<220> FEATURE:
<221> NAME/KEY: variation
<222> LOCATION: 35
<223> OTHER INFORMATION: /replace="a,g,c,t"

<400> SEQUENCE: 2
ggtaatacga ctcactatag cgagannnnn nnnnnccccc cccttt            47

<210> SEQ ID NO 3
<211> LENGTH: 45
<212> TYPE: DNA
<213> ORGANISM: Artificial Sequence
<220> FEATURE:
<223> OTHER INFORMATION: alternative RT primer
<220> FEATURE:
<221> NAME/KEY: variation
<222> LOCATION: 24
<223> OTHER INFORMATION: /replace="a,g,c,t"
<220> FEATURE:
<221> NAME/KEY: variation
<222> LOCATION: 25
<223> OTHER INFORMATION: /replace="a,g,c,t"
<220> FEATURE:
<221> NAME/KEY: variation
<222> LOCATION: 26
<223> OTHER INFORMATION: /replace="a,g,c,t"
<220> FEATURE:
<221> NAME/KEY: variation
<222> LOCATION: 27
<223> OTHER INFORMATION: /replace="a,g,c,t"
<220> FEATURE:
<221> NAME/KEY: variation
<222> LOCATION: 28
<223> OTHER INFORMATION: /replace="a,g,c,t"
<220> FEATURE:
<221> NAME/KEY: variation
<222> LOCATION: 29
<223> OTHER INFORMATION: /replace="a,g,c,t"
<220> FEATURE:
<221> NAME/KEY: variation
<222> LOCATION: 30
<223> OTHER INFORMATION: /replace="a,g,c,t"
<220> FEATURE:
<221> NAME/KEY: variation
<222> LOCATION: 31
<223> OTHER INFORMATION: /replace="a,g,c,t"
<220> FEATURE:
<221> NAME/KEY: variation
<222> LOCATION: 32
<223> OTHER INFORMATION: /replace="a,g,c,t"
<220> FEATURE:
<221> NAME/KEY: variation
<222> LOCATION: 33
<223> OTHER INFORMATION: /replace="a,g,c,t"
```

<400> SEQUENCE: 3
tgagtcggca gagaactggc gaannnnnnn nnncccccccc cctttt    45

<210> SEQ ID NO 4
<211> LENGTH: 24
<212> TYPE: DNA
<213> ORGANISM: Artificial Sequence
<220> FEATURE:
<223> OTHER INFORMATION: PCR primer reverse

<400> SEQUENCE: 4
ggtaatacga ctcactatag cgag    24

<210> SEQ ID NO 5
<211> LENGTH: 23
<212> TYPE: DNA
<213> ORGANISM: Artificial Sequence
<220> FEATURE:
<223> OTHER INFORMATION: alternative PCR primer reverse

<400> SEQUENCE: 5
tgagtcggca gagaactggc gaa    23

<210> SEQ ID NO 6
<211> LENGTH: 10
<212> TYPE: RNA
<213> ORGANISM: Unknown
<220> FEATURE:
<223> OTHER INFORMATION: poly(A)

<400> SEQUENCE: 6
aaaaaaaaaa    10

<210> SEQ ID NO 7
<211> LENGTH: 6
<212> TYPE: RNA
<213> ORGANISM: Artificial Sequence
<220> FEATURE:
<223> OTHER INFORMATION: GI tail
<220> FEATURE:
<221> NAME/KEY: variation
<222> LOCATION: 2
<223> OTHER INFORMATION: /replace="i"
<220> FEATURE:
<221> NAME/KEY: variation
<222> LOCATION: 4
<223> OTHER INFORMATION: /replace="i"
<220> FEATURE:
<221> NAME/KEY: variation
<222> LOCATION: 6
<223> OTHER INFORMATION: /replace="i"

<400> SEQUENCE: 7 gngngn    6

<210> SEQ ID NO 8
<211> LENGTH: 12
<212> TYPE: DNA
<213> ORGANISM: Unknown
<220> FEATURE:
<223> OTHER INFORMATION: sequence comprising a region complementary to a
      part of poly(A) and GI tail

<400> SEQUENCE: 8 tttcccccccc cc    12

```
<210> SEQ ID NO 9
<211> LENGTH: 3
<212> TYPE: DNA
<213> ORGANISM: unknown
<220> FEATURE:
<223> OTHER INFORMATION: complementary to isoTSO 3' end

<400> SEQUENCE: 9 ccc                                                                        3
```

FULL-LENGTH RNA SEQUENCING

CROSS-REFERENCE TO RELATED APPLICATION

This application is the U.S. national stage application of International Patent Application No. PCT/EP2019/071726, filed Aug. 13, 2019.

The Sequence Listing for this application is labeled "Seq-List.txt" which was created on Feb. 16, 2021 and is 4 KB. The entire content of the sequence listing is incorporated herein by reference in its entirety.

The present invention relates to the analysis of polyribonucleotides and in particular polyribonucleotides containing a 3' poly(A) tail such as messenger RNA (mRNA). The method can be used in the preparation of cDNA libraries and downstream sequencing. For example, the method according to the present invention enables sequencing of the entire molecule isoform together with the respective poly(A) tail of the source mRNA.

The present invention relates to a method for analyzing a polyribonucleotide, said method comprising the following steps: (a) obtaining a labeled polyribonucleotide by linking the 3' end of said polyribonucleotide and a random sequence of 1 to 20, preferably 1 to 5, G and I nucleotide residues; followed by (b) providing a second molecule comprising (b1) a first primer recognition sequence of 18 to 35 nucleotide residues in length that defines the 5' end of said second molecule, followed by (b2) a sequence of 5 to 15, preferably 8 to 10, C nucleotide residues linked to a sequence of 0 to 12, preferably 1 to 7, T nucleotide residues which define the 3' end of said second molecule, preferably a sequence of 9 C nucleotide residues linked to 3 T nucleotide residues; followed by (c) obtaining a complex of said labeled polyribonucleotide and said second molecule comprising a double-stranded sequence consisting of sequence (b2) of the second molecule and the complementary 3' end sequence of the labeled polyribonucleotide; followed by (d) obtaining an extended second molecule by (d1) extending the 3' end of the second molecule comprised in the complex obtained from step (c) by synthesizing a sequence that is complementary to the part of the sequence of the labeled polyribonucleotide which is not part of the double-stranded sequence comprised in the complex; followed by (d2) extending the 3' end of the second molecule obtained from step (d1) by adding at least (i) 1 to 5 C nucleotide residues, preferably 3 C nucleotide residues, followed by (ii) a second primer recognition sequence of 18 to 35 nucleotide residues in length.

Genetic information is stored as deoxyribonucleic acid (DNA) in the cell and can be transcribed into ribonucleic acid (RNA) when required. Both, DNA and RNA molecules, are built up of nucleotides consisting of a nitrogenous base, a five-carbon sugar, and at least one phosphate group. Different types of RNA molecules exist including mRNA molecules that carry the genetic information for protein synthesis. In eukaryotes, these mRNA molecules are transcribed from the DNA as pre-mature mRNA molecules and subsequently modified by adding for example a 3' polyadenosine (poly(A)) tail. The poly(A) tail is characteristic for mature, functional mRNA molecules with one of the few known exceptions being most histone mRNAs (Marzluff et al., 2008, Nat. Rev. Genet., 9(11):843-854; Yang et al., 2011, Genome Biology, 12:R16). The mature mRNA molecule is then transferred from the cell nucleus into the cytoplasm where it is translated into a protein. Thus, the DNA sequence as well as the amount, stability and translational efficiency of the mature mRNA molecule mainly determine the synthesis of the respective protein in a cell.

Gene expression, i.e. the use of genetic information stored in a cell, is crucial for the development and the physiology of organisms and their adaptation to changing environmental conditions. The regulation of gene expression happens at various levels, the most prominent being at the level of the RNA molecules, i.e. the transcription level. Aberrations in mRNA processing, affecting for instance splicing and alternative polyadenylation, have been associated with a plethora of diseases. In some cases, a direct mechanistic link between disease phenotype and the underlying dysregulation in gene expression has been used as target for treatment approaches. Several determinants of mRNA efficiency have been identified, investigated and modulated so far, including the efficiency of 5' capping, the nature of untranslated regions, the codon optimization of protein coding sequences, the presence of miRNA (microRNA) target sequences in the protein coding sequence and untranslated regions, and the length of the 3' polyadenosine (poly(A)) tail (e.g. Thess, et al., 2015, Mol. Ther., 23(9), 1456-1464; Trepotec et al., 2018, Tissue Engineering. Part A, ten.TEA.2017.0485; Ziemniak et al., 2013, Future Med. Chem., 5(10), 1141-1172). The poly(A) tail is involved in almost all key steps of RNA metabolism, including nuclear export, translation and stability (e.g. reviewed in Jalkanen et al., 2014, Semin Cell Dev Biol., 0: 24-32). However, although the length of the poly(A) tail is known to be one of the most important physiological factors influencing mRNA stability and translational efficiency, little is known to date in how far alterations in poly(A) tails length can influence and contribute to disease states and progression. Therefore, methods for querying at the genome-wide level the status of the poly(A) tail in combination with the respective mRNA sequence in high-throughput are required to understand the principles of mRNA regulation.

Most transcriptomic studies are based on microarrays or RNA sequencing so far (reviewed e.g. in Lowe et al., 2017, PLoS Comput Biol., 13(5):e1005457). In both cases, RNA molecules are commonly reverse transcribed in vitro into stable complementary DNA (cDNA) molecules as the mRNA molecules are rather unstable compared to DNA molecules. The obtained cDNA molecules or fragments thereof can then be investigated with respect to their nucleotide sequence and abundance. In case of microarrays the identification and quantification of mRNA molecules is facilitated by their immobilization on the array surface. Said surface comprises synthetic probes, i.e. nucleotide sequences with known sequence that are fixed on the microarray surface at known positions. cDNA molecules can hybridize with the probes in case they comprise a complementary nucleotide sequence and are thus immobilized on the array surface. However, a major drawback of microarray-based approaches is their limitation to a given set of preselected probes and thus, a limited number of cDNA molecules that can be investigated. On the other hand, RNA sequencing (RNA-seq) methods are commonly based on the investigation of short sequencing reads that are mapped to a, preferably well-annotated, reference sequence for computational reconstruction of the original RNA molecules. However, reference sequences are only available for a small number of species and of varying quality. In case of plant genomes for example the generation of high-quality reference genomes can be limited by short-read sequencing technologies due to the high amount of repetitive and transposable elements, presence-absence variations, copy number and gene content variations. Hence, RNA-seq methods enable high-throughput quantification of RNA molecules in a given sample as well as a detailed analysis of their respective nucleotide sequences, though bioinformatic analyses are complicated and prone to errors.

RNA-seq methods have been developed to measure the poly(A) tail length of mRNA molecules, in particular PAL-seq (Subtelny et al., 2014, Nature, 508(7494):66-71) and TAIL-seq (Chang et al., 2014, Mol Cell, 53(6):1044-52) and variants thereof. Both methods rely on the Illumina short-read sequencing technology to determine the average poly (A) tail length in a variety of biological samples with high throughput and accuracy and the availability of a well-annotated reference sequence. However, the short read length not only constrains the information regarding the mRNA isoform to which the measured poly(A) tail belongs, but can also misestimate poly(A) tail length, in particular in case of rather long poly(A) tails. For a correct estimation of the poly(A) tail length, the Illumina sequencing chemistry is changed in case of PAL-seq in order to introduce a biotin labeling of the poly(T) stretch in the cDNA molecule that can be detected with the fluorescent streptavidin. Thus, PAL-seq provides a fluorescent signal, the intensity of which is used as an estimate of the original poly(A) tail length. TAIL-seq, instead, uses the normal Illumina sequencing chemistry, but takes advantage of a dedicated base-calling algorithm that allows to detect the end of the poly(A) tail, thus also providing an estimate of the poly(A) tail length and the information necessary to assign the tail to its transcript of origin. Hence, both approaches are not straightforward to implement and require a tweaking of the Illumina sequencing chemistry or complex computational algorithms. Furthermore, both methods lack fundamental information with respect to the actual sequence of the poly(A) tail and the actual entire mRNA sequence to which the poly(A) tail belongs.

New sequencing methods were developed for example by Oxford Nanopore Technology Technologies® and Pacific Biosciences®, which constituted the so-called Third Generation Sequencing or long-read sequencing technologies, to overcome issues associated with the computational reconstruction of the original mRNA molecules in case of short-read sequencing approaches (reviewed e.g. in van Dijk et al., 2018, Trends Genet., 34 (9): 666-681). These methods are based on the generation of less, but much longer sequencing reads. Such reads comprise typically entire cDNAs, thereby circumventing problems associated with the computational reconstruction of original RNA molecules. Therefore, long-read sequencing technologies allow gathering combined information about transcription start, splicing and termination of a sequenced RNA molecule with high sensitivity and accuracy. However, research focused so far on the investigation of the part of an mRNA molecule that can be translated into proteins rather on a comprehensive investigation of mRNA molecules comprising such coding sequences as well as sequences that can affect the timing, duration and/or intensity of translation of a given mRNA molecule. In particular, current protocols are not optimized for simultaneously analyzing the entire sequences of mRNA isoforms in conjunction with their respective poly (A) tail transcriptome-wide. Hence, there is still a need to have at hand alternative solutions for determining the sequence of RNA molecules, in particular complete sequences of mRNA molecules including their respective poly (A) tails.

SUMMARY OF THE INVENTION

The present invention addresses the need for a simple and robust high-throughput method for investigating the entire sequence of polyribonucleotides and in particular polyribonucleotides containing a 3' poly(A) tail such as mRNA molecules, by providing the embodiments as recited in the claims.

In particular, the present invention relates to a method for analyzing a polyribonucleotide, said method comprising the following steps: (a) obtaining a labelled polyribonucleotide by linking the 3' end of said polyribonucleotide and a random sequence of 1 to 20, preferably 1 to 5, G and I nucleotide residues; followed by (b) providing a second molecule comprising (b1) a first primer recognition sequence of 18 to 35 nucleotide residues in length that defines the 5' end of said second molecule, followed by (b2) a sequence of 5 to 15, preferably 8 to 10, C nucleotide residues linked to a sequence of 0 to 12, preferably 1 to 7, T nucleotide residues which define the 3' end of said second molecule; followed by (c) obtaining a complex of said labelled polyribonucleotide and said second molecule comprising a double-stranded sequence consisting of sequence (b2) of the second molecule and the complementary 3' end sequence of the labelled polyribonucleotide; followed by (d) obtaining an extended second molecule by (d1) extending the 3' end of the second molecule comprised in the complex obtained from step (c) by synthesizing a sequence that is complementary to the part of the sequence of the labelled polyribonucleotide which is not part of the double-stranded sequence comprised in the complex; followed by (d2) extending the 3' end of the second molecule obtained from step (d1) by adding at least (i) 1 to 5 C nucleotide residues, followed by (ii) a second primer recognition sequence of 18 to 35 nucleotide residues in length. In other words, the present invention relates to a method for generating a cDNA library from a sample comprising a plurality of polyribonucleotides, preferably for high-throughput sequencing.

Hence, in short the method of the present invention in one important aspect comprises the following steps (e.g. as illustrated in FIG. 1):

1) optionally purifying and/or enriching polyribonucleotides of interest (RNAs, most notably lncRNAs and/or mRNAs with a poly(A) tail) of a sample,
2) "GI tailing" of the polyribonucleotides at their 3' ends (e.g. Kusov et al., 2001, Nucleic Acids Res., 29(12): E57-7; Patil et al., 2014, Methods Mol Biol., 1125:13-23),
3) priming first strand cDNA synthesis using a poly(C) containing "GI anchor oligonucleotide" (herein also called "first oligonucleotide") complementary to the GI tail created in step 2), wherein said anchor oligonucleotide preferably comprises a 3' overlap of T nucleotide (s) complementary to a part of the poly(A) tail in case the polyribonucleotides being mRNA molecules with a poly(A) tail, a first primer recognition sequence for downstream amplification (referred to as "3' handle" in FIG. 1) and optionally a random sequence (sometimes also referred to as a "unique molecular identifier (UMI) sequence") for downstream identification,
4) extending the generated first strand cDNA using a template switching oligonucleotide (TSO) (herein also called "second oligonucleotide") comprising isonucleotide containing nucleotide residues at its 5' end (therefore referred to as "isoTSO" in FIG. 1) (e.g. see Kapteyn et al., 2010, BMC Genomics 11:413) and a second primer recognition sequence for downstream amplification,
5) amplifying the cDNA molecules, preferably by PCR, using primers complementary to said primer recognition sequences to generate a cDNA library representing the poly(A) containing polyribonucleotides in the original sample, 6) optionally sequencing said cDNA library, preferably using a Third Generation cDNA sequencing method (e.g. PacBio or Nanopore discussed herein).

It has surprisingly been found that applying methods as described and claimed herein result in the accurate determination of the nucleotide sequence of polyribonucleotides including their poly(A) tails in case of mRNA molecules.

According to preferred aspects of the present invention, polyribonucleotides are obtained from a sample and elongated at one end with a GI tail consisting of a sequence of G and I nucleotides. Said GI tail is advantageous for subsequent reverse transcription of the polyribonucleotide into a more stable cDNA molecule that comprises a nucleotide sequence that is complementary to the ribonucleotide sequence of the polyribonucleotide and comprises in addition at one end a sequence complementary to said GI tail as well as nucleotide sequences that can be used for identification and/or PCR based amplification of the cDNA molecule at a later stage. Before amplification of the generated cDNA molecule the end of the cDNA molecule that does not comprise the nucleotide sequence complementary to said GI tail is further elongated by additional nucleotides that can be used for performing a template switch. Hence said end is further elongated by a nucleotide sequence complementary to a template switch oligonucleotide, herein also referred to a second oligonucleotide. Said second oligonucleotide comprises additional sequences that can be used for identification and/or PCR based amplification of the cDNA molecule while avoiding the generation of concatemers by the addition of a blocking sequence. A cDNA library can thus be generated based on said amplification sequences, i.e. primer recognition sequences using PCR and further investigated using a sequencing method such as a Third Generation sequencing method. Thus, long-read sequencing data can be obtained in high-throughput for entire polyribonucleotide sequences including mRNA molecules with a poly(A) tail.

Thus, the method is especially useful for investigating the entire nucleotide sequence of polyribonucleotides, in particular polyribonucleotide sequences containing a 3' poly(A) tail such as mRNAs. The method comprises the preparation of cDNA libraries and downstream sequencing. Hence, by applying the method information on mRNA abundance, its entire sequence, its precise poly(A) length and the full poly(A) tail internal sequence can be provided on a transcriptome-wide level with high precision, accuracy and reproducibility. In other words, the method according to the present invention enables the sequencing of the poly(A) tail of polyribonucleotides and the simultaneous determination of length and sequence composition of the poly(A) tails in conjunction with the respective mRNA isoform. Moreover, it was observed that comparatively low amounts of polyribonucleotides are required for such an analysis compared to the requirement of other technologies or methods.

DETAILED DESCRIPTION OF THE INVENTION

General Terms

Unless defined otherwise, all technical and scientific terms used herein have the same meaning as commonly understood by those skilled in the art to which the invention belongs. Although any methods and materials similar or equivalent to those described herein can be used in the practice or testing of the present invention, preferred methods and materials are described. For the purposes of the present invention, the following terms are defined below.

As used herein, "and/or" refers to and encompasses any and all possible combinations of one or more of the associated listed items, as well as the lack of combinations when interpreted in the alternative (or).

It will be understood that the term "between" when used in reference to a range of numerical values encompasses the numerical values at each endpoint of the range.

In the context of the present invention the term "sample" refers to biological samples including samples comprising biological cells and 3-dimensional aggregates comprising spatially organized cells such as, but not limited to organs and/or tissues. At least a fraction of said spatially organized cells may have a comparable morphology and/or may share comparable functions within the sample. The term "tissue" is intended to refer to an aggregate of cells of biological species, including, without being limited to plants, animals, and archaea, that are structurally and functionally organized. A tissue can comprise cells sharing similar functions and/or morphologies and thus, can be summarized as cell types that can perform specific functions. If obtained from a tissue such as for example a plant tissue, the source of the sample can be a solid as from a fresh, frozen and/or preserved tissue or organ.

Furthermore, a sample can be fluid such as, without being limited to, blood, urine, or saliva. In order to analyze polyribonucleotides according to the present invention, the sample might be pre-treated in order to isolate, purify and/or enrich said polyribonucleotides.

In the context of the present invention the term "sequencing" is intended to mean determining the identity of at least one nucleotide in a given nucleic acid molecule such as a DNA or RNA molecule, wherein less than all, a majority of all or all of the nucleotides in said molecule can be determined. With the method of the present invention, the full sequence of the polyribonucleotides in a sample including the sequence of poly(A) tails can be obtained by sequencing the corresponding cDNA library.

Polyribonucleotides and mRNA Molecules

In the context of the present invention, the term "polyribonucleotide" is a polynucleotide of at least 13 ribonucleotides, i.e. an RNA molecule, and is therefore used herein interchangeable with the term "RNA molecule" or just "RNA". Herein, the term "RNA" refers to single- or double-stranded RNA molecules, preferably single-stranded RNA molecules built up of A, C, G, and/or U nucleotides or modification of those. Herein, the term "nucleotide" is used interchangeable with the term "nucleotide residue" and refers to nucleotides (i.e. desoxyribonucleotides) in case of DNA and cDNA molecules and to ribonucleotides in case of RNA molecules. A, C, G, T and U nucleotides refer to nucleotides comprising adenine, guanine, cytosine, thymine, and uracil as the respective nitrogenous base. Hence, the term "polyribonucleotide" comprises any molecule build up of RNA, i.e. build up of A, C, G, and/or U nucleotides, including coding and non-coding RNA molecules. Different types of RNA molecules exist including, but not limited to mRNA, lncRNAs, circular RNAs, miRNAs, snoRNAs, tRNAs, snRNAs and siRNAs.

According to the present invention preferably RNA molecules are analyzed which are selected from the group consisting of mRNA, lncRNAs, miRNAs, snoRNAs, snRNAs, tRNAs and siRNAs, preferably mRNAs and lncRNAs. The term "I nucleotide" refers to an inosine nucleotide, i.e.

in the case of a cDNA or a DNA oligonucleotide a desoxyribonucleotide comprising inosine as the base.

In particularly preferred embodiments, a polyribonucleotide is an mRNA or lncRNA molecule, preferably an mRNA molecule with a poly(A) tail. In other words, in particularly preferred embodiments, a transcriptome is analyzed.

In the context of the present invention, the term "mRNA" refers to an RNA molecule that comprises a part that that can be translated into a protein. In other words, the term "mRNA" should be understood to mean any RNA molecule which is suitable for the expression of an amino acid sequence or which is translatable into an amino acid sequence such as a protein. The term "lncRNA" refers to an at least 200 nucleotides long, non-coding RNA, which is an RNA molecule sharing the same synthesis machinery and sequence features of an mRNA, but not translated into a protein.

In eukaryotes, mRNA and lncRNA molecules are synthesized from their 5' to their 3' end as pre-mature mRNA and lncRNA molecules during transcription and enzymatically processed into mature mRNA and lncRNA molecules, respectively. Such processing steps can refer to the addition of a 5' cap, splicing, and/or the addition of a 3' poly(A) tail. Hence, RNA molecules comprised in a biological sample to be analyzed can comprise pre-mature and/or mature mRNA and/or lncRNA molecules, wherein pre-mature mRNA molecules also include mRNA molecules during processing and wherein pre-mature lncRNA molecules also include lncRNA molecules during processing.

Preferably, lncRNA molecules and mRNA molecules with a poly(A) tail are analyzed using the method according to the present invention.

In case of the polyribonucleotide to be analyzed is an mRNA molecule with a poly(A) tail, said polyribonucleotide comprises at least a coding sequence and a 3' poly(A) tail, preferably in addition a 5' and/or a 3' untranslated region (UTR). In other words, the polyribonucleotide is preferably an mRNA molecule comprising preferably a 5' UTR, followed by a coding sequence, preferably followed by a 3' UTR, followed by a poly(A) tail.

The 5' end of the 5' UTR is defined by the transcriptional start site and its 3' end is followed by the coding sequence. The coding sequence is terminated by the start and the stop codon, i.e. the first and the last three nucleotides of the mRNA molecule that can be translated, the "open reading frame", respectively. The 3' UTR starts after the stop codon of the coding sequence and is followed by a poly(A) tail.

The coding sequence comprises codons that can be translated into an amino acid sequence such as a protein. In other words, by "coding sequence" is meant any nucleic acid sequence that contributes to the code for the polypeptide product of a gene. By contrast, the term "non-coding sequence" refers to any nucleic acid sequence that may comprise regulatory elements but does not contribute to the code for the polypeptide product of a gene.

The coding sequence can contain the codons of a naturally occurring coding sequence or it can be a partially or completely synthetic coding sequence. Alternatively, the coding sequence can be a partly or fully codon optimized sequence derived from the natural sequence to be used. Most of the amino acids are encoded by more than one codon, i.e. three consecutive nucleotides of an mRNA molecule that can be translated into an amino acid. Codons exist that are used preferentially in some species for a given amino acid. The presence of more often occurring codons can enhance the amount of amino acid sequences translated based on a given mRNA molecule compared to the same mRNA molecule but comprising comparably rare codons.

As regards the function of the encoded amino acid sequence, there is no limitation and possible amino acid sequences to be encoded by said polyribonucleotide are described further below. Herein, the term "amino acid sequence" encompasses any kind of amino acid sequence, i.e. chains of two or more amino acids which are each linked via peptide bonds and refers to any amino acid sequence of interest. Preferably, the encoded amino acid sequence is at least 5 amino acids long, more preferably at least 10 amino acids, even more preferably at least 50, 100, 200 or 500 amino acids. In other words, the term "amino acid sequence" covers short peptides, oligopeptides, polypeptides, fusion proteins, proteins as well as fragments thereof, such as parts of known proteins, preferably functional parts. These can, for example be biologically active parts of a protein or antigenic parts such as epitopes which can be effective in raising antibodies.

The poly(A) tail comprises a nucleotide sequence consisting of A nucleotides. In eukaryotes, a large fraction of naturally occurring poly(A) tails exhibits a length between 20 and 150 A nucleotides. Optionally, the polyribonucleotide can comprise in addition one or more nucleotides other than A nucleotides such as interspersed and/or 3' terminal C, G, and/or G nucleotides. For example, one or more 3' terminal G nucleotides can be comprised in a poly(A) tail.

The mRNA molecule can optionally comprise in addition a 5' and/or a 3' UTR. An UTR can comprise one or more regulatory sequences such as a binding site for protein that enhances or impairs the stability of the mRNA molecule, a binding site for a regulatory RNA molecule such as a miRNA molecule, and/or a signal sequence involved in intracellular transport of the mRNA molecule.

An mRNA molecule to be analyzed using the method according to the present invention can optionally comprise in addition a 5' cap such as a C1-m7G cap or an m7GpppG cap.

In preferred embodiments, the polyribonucleotides are extracted from a sample such as one or more cells and purified for analyses as described below, i.e. separated from other cellular components like for example amino acid sequences such as proteins.

In particularly preferred embodiments, the polyribonucleotides are lncRNA molecules and/or mRNA molecules with a poly(A) tail that are enriched for analyses as described below. In other words, lncRNA molecules and/or mRNA or having a poly(A) tail are preferably obtained by extraction and purification of polyribonucleotides from a sample followed by an enrichment step based for example on said poly(A) tail sequence. Thus, preferably ribodepleted and/or poly(A) tail enriched polyribonucleotides are investigated as described below. "Ribodepleted" RNA is the result of removing ribosomal RNA (rRNA) from total RNA, thus, enriching RNA molecules such as mRNA molecules. Ribodepletion (i.e. the removal of rRNA) can, e.g., be achieved by using rRNA binding probes such as the locked nucleic acid (LNA®) based probes in the RiboMinus™ kits commercially available from ThermoFisher Scientific (Waltham, Massachusetts, U.S.A.).

The method according to the present invention is schematically shown in FIG. 1 with the steps being described in the following.

In particular, the present invention relates to a method for analyzing a polyribonucleotide, said method comprising the following steps: (a) obtaining a labelled polyribonucleotide by linking the 3' end of said polyribonucleotide and a random sequence of 1 to 20, preferably 1 to 5, G and I nucleotide residues; followed by (b) providing a second molecule comprising (b1) a first primer recognition sequence of 18 to 35 nucleotide residues in length that defines the 5' end of said second molecule, followed by (b2) a sequence of 5 to 15, preferably 8 to 10, C nucleotide residues linked to a sequence of 0 to 12, preferably 1 to 7, T nucleotide residues which define the 3' end of said second molecule; followed by (c) obtaining a complex of said labelled polyribonucleotide and said second molecule comprising a double-stranded sequence consisting of sequence (b2) of the second molecule and the complementary 3' end sequence of the labelled polyribonucleotide; followed by (d) obtaining an extended second molecule by (d1) extending the 3' end of the second molecule comprised in the complex obtained from step (c) by synthesizing a sequence that is complementary to the part of the sequence of the labelled polyribonucleotide which is not part of the double-stranded sequence comprised in the complex; followed by (d2) extending the 3' end of the second molecule obtained from step (d1) by adding at least (i) 1 to 5 C nucleotide residues, followed by (ii) a second primer recognition sequence of 18 to 35 nucleotide residues in length.

In other words, the present invention relates to a method for generating a cDNA library from a sample comprising a plurality of polyribonucleotides, preferably for high-throughput sequencing. Said polyribonucleotides preferably comprise or more preferably consist of lncRNA molecules and/or mRNA molecules with a poly(A) tail.

GI Tailing

According to the present invention, a labeled polyribonucleotide is obtained by linking the 3' end of said polyribonucleotide and a random sequence of 1 to 20, preferably 1 to 5, G and I nucleotide residues.

In other words, the polyribonucleotide is labeled by adding a random sequence of in total 1 to 20, preferably 1 to 5, G and I nucleotides to its 3' end. This range refers to the total amount of G and I residues included.

It can also be said that the 3' end of the polyribonucleotide is enzymatically elongated with a random sequence of 1 to 20, preferably 1 to 5, G and I nucleotide residues.

As mentioned herein above, the term "I nucleotide" refers to an inosine nucleotide, i.e. a nucleotide having an inosine as a nitrogenous base.

The procedure of adding a nucleotide sequence of G and I nucleotides to a given nucleotide sequence is also referred to as GI tailing (c.f. Kusov et al., 2001, Nucleic Acids Res., 29(12):E57-7; Patil et al., 2014, Methods Mol Biol., 1125: 13-23). GI tailing is particularly advantageous to create a nucleotide sequence that can be used as a priming site for reverse transcription.

In preferred embodiments, the GI tailing sequence consists of 1 G or 1 I nucleotide.

In preferred embodiments, the GI tailing sequence is a random nucleotide sequence consisting of 2 G nucleotides, 1 G and 1 I nucleotide, or 2 I nucleotides.

In preferred embodiments, the GI tailing sequence is a random nucleotide sequence consisting of 3 G nucleotides, 2 G and 1 I nucleotides, 1 G and 2 I nucleotides, or 3 I nucleotides.

In preferred embodiments, the GI tailing sequence is a random nucleotide sequence consisting of 4 G nucleotides, 3 G and 1 I nucleotides, 2 G and 2 I nucleotides, 1 G and 3 I nucleotides, or 4 I nucleotides.

In preferred embodiments, the GI tailing sequence is a random nucleotide sequence consisting of 5 G nucleotides, 4 G and 1 I nucleotides, 3 G and 2 I nucleotides, 2 G and 3 I nucleotides, 1 G and 4 I nucleotides, or 5 I nucleotides.

In some embodiments, the GI tailing sequence is a random nucleotide sequence consisting of 6 G nucleotides, 5 G and 1 I nucleotides, 4 G and 2 I nucleotides, 3 G and 3 I nucleotides, 2 G and 4 I nucleotides, 1 G and 5 I nucleotides, or 6 I nucleotides.

In some embodiments, the GI tailing sequence is a random nucleotide sequence consisting of 7 G nucleotides, 6 G and 1 I nucleotides, 5 G and 2 I nucleotides, 4 G and 3 I nucleotides, 3 G and 4 I nucleotides, 2 G and 5 I nucleotides, 1 G and 6 I nucleotides, or 7 I nucleotides.

In some embodiments, the GI tailing sequence is a random nucleotide sequence consisting of 8 G nucleotides, 7 G and 1 I nucleotides, 6 G and 2 I nucleotides, 5 G and 3 I nucleotides, 4 G and 4 I nucleotides, 3 G and 5 I nucleotides, 2 G and 6 I nucleotides, 1 G and 7 I nucleotides, or 8 I nucleotides.

In some embodiments, the GI tailing sequence is a random nucleotide sequence consisting of 9 G nucleotides, 8 G and 1 I nucleotides, 7 G and 2 I nucleotides, 6 G and 3 I nucleotides, 5 G and 4 I nucleotides, 4 G and 5 I nucleotides, 3 G and 6 I nucleotides, 2 G and 7 I nucleotides, 1 G and 8 I nucleotides, or 9 I nucleotides.

In some embodiments, the GI tailing sequence is a random nucleotide sequence consisting of 10 G nucleotides, 9 G and 1 I nucleotides, 8 G and 2 I nucleotides, 7 G and 3 I nucleotides, 6 G and 4 I nucleotides, 5 G and 5 I nucleotides, 4 G and 6 I nucleotides, 3 G and 7 I nucleotides, 2 G and 8 I nucleotides, 1 G and 9 I nucleotides, or 10 I nucleotides.

In some embodiments, the GI tailing sequence is a random nucleotide sequence consisting of 11 G nucleotides, 10 G and 1 I nucleotides, 9 G and 2 I nucleotides, 8 G and 3 I nucleotides, 7 G and 4 I nucleotides, 6 G and 5 I nucleotides, 5 G and 6 I nucleotides, 4 G and 7 I nucleotides, 3 G and 8 I nucleotides, 2 G and 9 I nucleotides, 1 G and 10 I nucleotides, or 11 I nucleotides.

In some embodiments, the GI tailing sequence is a random nucleotide sequence consisting of 12 G nucleotides, 11 G and 1 I nucleotides, 10 G and 2 I nucleotides, 9 G and 3 I nucleotides, 8 G and 4 I nucleotides, 7 G and 5 I nucleotides, 6 G and 6 I nucleotides, 5 G and 7 I nucleotides, 4 G and 8 I nucleotides, 3 G and 9 I nucleotides, 2 G and 10 I nucleotides, 1 G and 11 I nucleotides, or 12 I nucleotides.

In some embodiments, the GI tailing sequence is a random nucleotide sequence consisting of 13 G nucleotides, 12 G and 1 I nucleotides, 11 G and 2 I nucleotides, 10 G and 3 I nucleotides, 9 G and 4 I nucleotides, 8 G and 5 I nucleotides, 7 G and 6 I nucleotides, 6 G and 7 I nucleotides, 5 G and 8 I nucleotides, 4 G and 9 I nucleotides, 3 G and 10 I nucleotides, 2 G and 11 I nucleotides, 1 G and 12 I nucleotides, or 13 I nucleotides.

In some embodiments, the GI tailing sequence is a random nucleotide sequence consisting of 14 G nucleotides, 13 G and 1 I nucleotides, 12 G and 2 I nucleotides, 11 G and 3 I nucleotides, 10 G and 4 I nucleotides, 9 G and 5 I nucleotides, 8 G and 6 I nucleotides, 7 G and 7 I nucleotides, 6 G and 8 I nucleotides, 5 G and 9 I nucleotides, 4 G and 10 I nucleotides, 3 G and 11 I nucleotides, 2 G and 12 I nucleotides, 1 G and 13 I nucleotides, or 14 I nucleotides.

In some embodiments, said GI tailing sequence is a random nucleotide sequence consisting of 15 G nucleotides, 14 G and 1 I nucleotides, 13 G and 2 I nucleotides, 12 G and 3 I nucleotides, 11 G and 4 I nucleotides, 10 G and 5 I nucleotides, 9 G and 6 I nucleotides, 8 G and 7 I nucleotides, 7 G and 8 I nucleotides, 6 G and 9 I nucleotides, 5 G and 10 I nucleotides, 4 G and 11 I nucleotides, 3 G and 12 I nucleotides, 2 G and 13 I nucleotides, 1 G and 14 I nucleotides, or 15 I nucleotides.

In some embodiments, the GI tailing sequence is a random nucleotide sequence consisting of 16 G nucleotides, 15 G and 1 I nucleotides, 14 G and 2 I nucleotides, 13 G and 3 I nucleotides, 12 G and 4 I nucleotides, 11 G and 5 I nucleotides, 10 G and 6 I nucleotides, 9 G and 7 I nucleotides, 8 G and 8 I nucleotides, 7 G and 9 I nucleotides, 6 G and 10 I nucleotides, 5 G and 11 I nucleotides, 4 G and 12 I nucleotides, 3 G and 13 I nucleotides, 2 G and 14 I nucleotides, 1 G and 15 I nucleotides, or 16 I nucleotides.

In some embodiments, the GI tailing sequence is a random nucleotide sequence consisting of 17 G nucleotides, 16 G and 1 I nucleotides, 15 G and 2 I nucleotides, 14 G and 3 I nucleotides, 13 G and 4 I nucleotides, 12 G and 5 I nucleotides, 11 G and 6 I nucleotides, 10 G and 7 I nucleotides, 9 G and 8 I nucleotides, 8 G and 9 I nucleotides, 7 G and 10 I nucleotides, 6 G and 11 I nucleotides, 5 G and 12 I nucleotides, 4 G and 13 I nucleotides, 3 G and 14 I nucleotides, 2 G and 15 I nucleotides, 1 G and 16 I nucleotides, or 17 I nucleotides.

In some embodiments, the GI tailing sequence is a random nucleotide sequence consisting of 18 G nucleotides, 17 G and 1 I nucleotides, 16 G and 2 I nucleotides, 15 G and 3 I nucleotides, 14 G and 4 I nucleotides, 13 G and 5 I nucleotides, 12 G and 6 I nucleotides, 11 G and 7 I nucleotides, 10 G and 8 I nucleotides, 9 G and 9 I nucleotides, 8 G and 10 I nucleotides, 7 G and 11 I nucleotides, 6 G and 12 I nucleotides, 5 G and 13 I nucleotides, 4 G and 14 I nucleotides, 3 G and 15 I nucleotides, 2 G and 16 I nucleotides, 1 G and 17 I nucleotides, or 18 I nucleotides.

In some embodiments, the GI tailing sequence is a random nucleotide sequence consisting of 19 G nucleotides, 18 G and 1 I nucleotides, 17 G and 2 I nucleotides, 16 G and 3 I nucleotides, 15 G and 4 I nucleotides, 14 G and 5 I nucleotides, 13 G and 6 I nucleotides, 12 G and 7 I nucleotides, 11 G and 8 I nucleotides, 10 G and 9 I nucleotides, 9 G and 10 I nucleotides, 8 G and 11 I nucleotides, 7 G and 12 I nucleotides, 6 G and 13 I nucleotides, 5 G and 14 I nucleotides, 4 G and 15 I nucleotides, 3 G and 16 I nucleotides, 2 G and 17 I nucleotides, 1 G and 18 I nucleotides, or 19 I nucleotides.

In some embodiments, the GI tailing sequence is a random nucleotide sequence consisting of 20 G nucleotides, 19 G and 1 I nucleotides, 18 G and 2 I nucleotides, 17 G and 3 I nucleotides, 16 G and 4 I nucleotides, 15 G and 5 I nucleotides, 14 G and 6 I nucleotides, 13 G and 7 I nucleotides, 12 G and 8 I nucleotides, 11 G and 9 I nucleotides, 10 G and 10 I nucleotides, 9 G and 11 I nucleotides, 8 G and 12 I nucleotides, 7 G and 13 I nucleotides, 6 G and 14 I nucleotides, 5 G and 15 I nucleotides, 4 G and 16 I nucleotides, 3 G and 17 I nucleotides, 2 G and 18 I nucleotides, 1 G and 19 I nucleotides, or 20 I nucleotides.

The length of the GI tailing sequence, i.e. the random sequence consisting of 1 to 20, preferably of 1 to 5, G and I nucleotides added to the polyribonucleotide under study, can be determined by various methods known to the person skilled in the art such as polyacrylamide gel electrophoresis (PAGE) or using the USB polyA length assay kit (ThermoFisher) as described in the appended Examples.

GI tailing is preferably done enzymatically by using a poly(A) polymerase (PAP), more preferably by using a PAP from yeast. Typically, *Escherichia coli* and yeast PAPs are commercially available. However, PAPs obtained from yeast are more error-prone compared to other PAPs such as from *Escherichia coli*. As a consequence, PAPs from yeast add G and/or I nucleotides more efficiently than other PAPs such as from *Escherichia coli*. Thus, in a particularly preferred embodiment, PAPs from yeast are used. For ensuring that a GI tail consisting of G and I nucleotides is added to the polyribonucleotides, GI tailing is preferably done enzymatically in the presence of only G and I nucleotides.

Hence, in preferred embodiments, the 3' end of a polyribonucleotide is enzymatically elongated with a random sequence of 1 to 20, preferably 1 to 5, G and I nucleotide residues, preferably in the presence of G and I nucleotides.

In particularly preferred embodiments, the 3' end of a polyribonucleotide is elongated with a random sequence of 1 to 20, preferably 1 to 5, G and I nucleotide residues using a PAP from yeast, preferably in the presence of G and I nucleotides.

In preferred embodiments, the polyribonucleotide is a lncRNA molecule and a labeled lncRNA molecule is obtained by adding a random sequence of in total 1 to 20 G and I nucleotides to the 3' end of the lncRNA molecule. In other words, in a preferred embodiment, the polyribonucleotide is a lncRNA molecule and the 3' end of the lncRNA molecule is enzymatically elongating with a random sequence of 1 to 20 G and I nucleotide residues.

In preferred embodiments, the polyribonucleotide is an mRNA molecule and a labeled mRNA molecule is obtained by adding a random sequence of in total 1 to 20 G and I nucleotides to the 3' end of the poly(A) tail of the mRNA molecule. In other words, in a preferred embodiment, the polyribonucleotide is an mRNA molecule and the 3' end of the mRNA molecule is enzymatically elongating with a random sequence of 1 to 20 G and I nucleotide residues.

In particularly preferred embodiments, the polyribonucleotide is a lncRNA molecule and a labeled lncRNA molecule is obtained by adding a random sequence of in total 1 to 5 G and I nucleotides to the 3' end of the lncRNA molecule. In other words, in a preferred embodiment, the polyribonucleotide is a lncRNA molecule and the 3' end of the lncRNA molecule is enzymatically elongating with a random sequence of 1 to 5 G and I nucleotide residues.

In particularly preferred embodiments, the polyribonucleotide is an mRNA molecule and a labeled mRNA molecule is obtained by adding a random sequence of in total 1 to 5 G and I nucleotides to the 3' end of the poly(A) tail of the mRNA molecule. In other words, in particularly preferred embodiments, the polyribonucleotide is an mRNA molecule and the 3' end of the mRNA molecule is enzymatically elongating with a random sequence of 1 to 5 G and I nucleotide residues.

Second Molecule/First Oligonucleotide

According to the present invention, the step of GI tailing is followed by the step of providing a second molecule comprising (b1) a first primer recognition sequence of 18 to 35 nucleotide residues in length that defines the 5' end of said second molecule, followed by (b2) a sequence of 5 to 15, preferably 8 to 10, C nucleotide residues linked to a sequence of 0 to 12, preferably 1 to 7, T nucleotide residues which define the 3' end of said second molecule. In other words, said second molecule is a single-stranded nucleotide sequence that comprises a first primer recognition site that is followed by C nucleotides which can in turn be followed by T nucleotides. Hence, said second molecule can also be referred to as a first oligonucleotide herein.

In the context of the present invention, the term "primer recognition sequence" refers to a nucleotide sequence consisting of 18 to 35 nucleotides in length. Such a primer recognition sequence refers to a common nucleotide sequence for enabling binding of short single-stranded oligonucleotides, i.e. primers. Herein, said primer recognition sequences are recognition sequences enabling reverse transcription which requires short primers for synthesis of the single-strand cDNA, in particular the first strand cDNA having a sequence complementary to the respective polyribonucleotide sequence. In principle, any random sequence consisting of 18 to 35 nucleotides that is not present in the polyribonucleotide under study may work reasonably well.

Herein, the term "complementary" refers to nucleotides the nitrogenous bases of which can naturally bind to each other by hydrogen bonds, i.e. A and T nucleotides, A and U nucleotides as well as C and G nucleotides.

Herein, the term "hybridization" refers to the naturally occurring binding of nucleotides to each other by the formation of hydrogen bonds between their respective nitrogenous bases. Hence, two at least partially complementary single-stranded nucleotide sequences can form at least partially a double-stranded nucleotide sequence due to the formation of hydrogen bonds between the respective nitrogenous bases as described above. Thus, the term "hybridization" is intended to be understood as "base-pairing" and can thus be read interchangeable with "base-pairing".

The second molecule according to the present invention comprises 0 to 12 T nucleotides, preferably 1 to 7 T nucleotides which define the 3' end of said second molecule. The absence of T nucleotides in said second molecule is advantageous for example in case polyribonucleotides such as mRNA molecules with a poly(A) tail ending with at least one terminal nucleotide other than an A nucleotide, and/or lncRNA molecules are investigated. The presence of T nucleotides in said second molecule is advantageous in case mRNA molecules with a poly(A) tail ending with at least one terminal A nucleotide are investigated. Hence, the presence of 1 to 12, preferably of 1 to 7, T nucleotides in said second molecule is preferred for the analysis of mRNA molecules with a standard poly(A) tail. However, the presence of more than 12 T nucleotides that define the 3' end of said second molecule is not preferred.

In some embodiments, the first primer recognition sequence consists of 18 to 35 nucleotide residues and is followed by a sequence of 5 to 15 C nucleotide residues linked to a sequence of 0 to 12 T nucleotide residues. In other words, said second molecule comprises in 5' to 3' direction a first primer recognition sequence of 18 to 35 nucleotide residues in length, 5 to 15 C nucleotide residues, and 0 to 12 T nucleotide residues. The part of said second molecule that consists of said 5 to 15 C nucleotide residues linked to 0 to 12 T nucleotide residues allows hybridization of said second molecule to a polyribonucleotide, preferably to the 3' end of an mRNA molecule and the poly(A) tail linked to it.

In preferred embodiments, the first primer recognition sequence consists of 18 to 35 nucleotide residues and is followed by a sequence of 8 to 10 C nucleotide residues linked to a sequence of 1 to 7 T nucleotide residues which define the 3' end of said second molecule. Hence, said first primer recognition sequence is covalently linked to a sequence consisting of 8, 9, or 10 C nucleotides that is covalently linked at the other end to a sequence of 1, 2, 3, 4, 5, 6 or 7 T nucleotides. In other words, said second molecule comprises in 5' to 3' direction a first primer recognition sequence of 18 to 35 nucleotide residues in length, 8 to 10 C nucleotide residues, and 1 to 7 T nucleotide residues. The part of said second molecule that consists of said 8 to 10 C nucleotide residues linked to 1 to 7 T nucleotide residues is allows hybridization of said second molecule to a polyribonucleotide, preferably to the 3' end of an mRNA molecule and the poly(A) tail linked to it.

In some embodiments, said second molecule, i.e. said first oligonucleotide, comprises in addition a first identifier sequence of 6 to 12, preferably 10, random nucleotide residues in length between the first primer recognition sequence and the 5 to 15, preferably 8 to 10 C nucleotide residues that are linked to 0 to 12, preferably 1 to 7 T nucleotide residues.

In other words, the second molecule, i.e. the first oligonucleotide, comprises a first primer recognition sequence of 18 to 35 nucleotide residues in length that defines the 5' end of said second molecule, followed by a first identifier sequence of 6 to 12, preferably 10, random nucleotide residues in length, followed by a sequence of 5 to 15, preferably 8 to 10, C nucleotide residues linked to a sequence of 0 to 12, preferably 1 to 7, T nucleotide residues which define the 3' end of said second molecule, i.e. said first oligonucleotide.

Herein, the term "identifier sequence" refers to a nucleotide sequence that is unique for each given polyribonucleotide molecule in the sample under investigation. However, there can also be sample specific barcode sequences instead or in addition to the molecule specific identifiers. Identifier sequences are also referred to as "unique molecular identifier" (UMI) (e.g. in the Illumina systems). Such identifier sequences enable the parallel investigation of polyribonucleotides, preferably lncRNA molecules and/or mRNA molecules with a poly(A) tail, of several samples such as for example in a single sequencing run. Hence, unique identifier sequences can enable cost-efficient analyses in high-throughput.

Complex/Hybridization

According to the present invention, the step of providing a second molecule is followed by the step of obtaining a complex of said labeled polyribonucleotide and said second molecule comprising a double-stranded sequence consisting of i) the 5 to 15, preferably 8 to 10, C nucleotide residues linked to the sequence of 0 to 12, preferably 1 to 7, T nucleotide residues of the second molecule, and ii) the complementary 3' end sequence of the labeled polyribonucleotide.

In other words, the labelled polyribonucleotide is contacted with said second molecule, i.e. said first oligonucleotide, allowing hybridization of said second molecule, i.e. said first oligonucleotide, to said polyribonucleotide.

Reverse Transcription

According to the present invention, the step of complex formation is followed by the step of obtaining an extended second molecule by first extending the 3' end of the second molecule comprised in the complex by synthesizing a sequence that is complementary to the part of the sequence of the labeled polyribonucleotide which is not part of the double-stranded sequence comprised in the complex.

In other words, the hybridized first oligonucleotide is enzymatically elongated using a reverse transcriptase enzyme, wherein said polyribonucleotides serve as the template, thereby generating the first strand of cDNA.

Examples for suitable reverse transcriptase enzyme include, without being limited to, MMLV reverse transcriptase, RNase H minus (cat. M3681, Promega), Superscript II (18064014, Thermo Fisher), Superscript III (18080093, Thermo Fisher), and SMRTScribe reverse transcriptase (cat. 639538, Takara).

Template Switching

According to the present invention, the step of obtaining an extended second molecule comprises next extending the new obtained 3' end of the second molecule by adding at least (i) 1 to 5, preferably 3, C nucleotide residues, followed by (ii) a second primer recognition sequence of 18 to 35 nucleotide residues in length.

In other words, the procedure as described in the following is performed.

Elongation of the cDNA Strand, Part I

According to the present invention, said hybridized first oligonucleotides are enzymatically elongated using a reverse transcriptase enzyme, wherein said polyribonucleotides serve as the template, thereby generating the first strand of cDNA the 3' end of which is then enzymatically elongated with 1 to 5 nucleotide residues, preferably 1 to 5 C nucleotides, more preferably 3 C nucleotide residues. In other words, the 3' end of the generated first cDNA strand is enzymatically elongated with 1 to 5 nucleotide residues, preferably 1 to 5 C nucleotides, more preferably 3 C nucleotide residues, so as to allow hybridization of second oligonucleotides to said polyribonucleotides in said sample.

Hence, in particularly preferred embodiments, the 3' end of said first cDNA strand is enzymatically elongated with 1 to 5 C nucleotides, preferably 3 C nucleotide residues, so as to allow hybridization of second oligonucleotides to said polyribonucleotides in said sample. In other words, 1 to 5, preferably 3, C nucleotides are incorporated in the first cDNA strand.

Second Oligonucleotide

According to the present invention, the sample under study is contacted with a plurality of said second oligonucleotides comprising in 5' to 3' direction (i) a blocking sequence, preferably consisting of 1 to 5 isomeric nucleotide residues, more preferably of 3 isomeric C nucleotide residues or of 1 isomeric G nucleotide residue flanked by 2 isomeric C nucleotide residues, (ii) a second primer recognition sequence of 18 to 35 nucleotide residues in length, (iii) optionally 1 to 5, preferably 3, ribo-G nucleotide residues complementary to the C nucleotide residues incorporated in the first cDNA strand.

In the context of the present invention, such second oligonucleotides refer in particular to template switching oligonucleotides. Hence, said second oligonucleotides are preferably template switching oligonucleotides (e.g. as in Kapteyn et al., 2010, BMC Genomics 11:413).

Herein, the term "blocking sequence" refers to any nucleotide sequence comprising a modification that causes the termination of reverse transcription. In other words, any modification that results in blocking the reverse transcriptase is possible, such as for example a nucleotide sequence building a secondary structure such as a hairpin loop or a nucleotide sequence that consists of or comprises modified nucleotides such as isomeric nucleotides. Isomeric nucleotides are preferred introducing a road-block to reverse transcription by forming non-standard base pairing. Such a road-block may thus be achieved by any modification that does not allow efficient base-pairing. A blocking sequence is advantageous to avoid concatemer extension of first and second oligonucleotides.

In preferred embodiments, said blocking sequence consists of 1 to 5 isomeric nucleotide residues.

In particularly preferred embodiments, said blocking sequence consists of 3 isomeric C nucleotide residues or of 1 isomeric G nucleotide residue flanked by 2 isomeric C nucleotide residues.

Herein, the term "isomeric nucleotide residue" refers to isomers of nucleotides having the same chemical formula, but having differently arranged atoms. In particularly preferred embodiments of the present invention the isomeric nucleotides are isomeric C and/or G nucleotides. Isomeric cytosine and guanine nitrogenous bases are shown in FIG. 2.

Hence, in some embodiments, said labeled and hybridized polyribonucleotides, preferably mRNA molecules, are contacted with a plurality of second oligonucleotides comprising in 5' to 3' direction a blocking sequence consisting of 1 to 5 isomeric nucleotide residues, followed by a second primer recognition sequence of 18 to 35 nucleotide residues in length.

In preferred embodiments, said labeled and hybridized polyribonucleotides, preferably mRNA molecules, are contacted with a plurality of second oligonucleotides comprising in 5' to 3' direction a blocking sequence consisting of 3 isomeric C nucleotide residues or of 1 isomeric G nucleotide residue flanked by 2 isomeric C nucleotide residues, followed by a second primer recognition sequence of 18 to 35 nucleotide residues in length.

In particularly preferred embodiments, said labeled and hybridized polyribonucleotides, preferably mRNA molecules, are contacted with a plurality of second oligonucleotides comprising in addition at the 3' end 1 to 5, preferably 3, ribo-G nucleotide residues complementary to the C nucleotide residues incorporated in the first cDNA strand so as to allow hybridization of said second oligonucleotides to said first cDNA strands. In other words, in particularly preferred embodiments, said labeled and hybridized polyribonucleotides, preferably mRNA molecules, are contacted with a plurality of second oligonucleotides comprising in 5' to 3' direction (i) a blocking sequence consisting of 3 isomeric C nucleotide residues or of 1 isomeric G nucleotide residue flanked by 2 isomeric C nucleotide residues, (ii) a second primer recognition sequence of 18 to 35 nucleotide residues in length, and (iii) 1 to 5, preferably 3, ribo-G nucleotide residues complementary to the C nucleotide residues incorporated in the first cDNA strand so as to allow hybridization of said second oligonucleotides to said first cDNA strands.

The oligonucleotides (first and second oligonucleotides, i.e. "GI anchor oligonucleotide" and "isoTSO") used for priming the first strand cDNA synthesis and used as a template during said first strand cDNA synthesis, respectively, as well as primers and/or probes used for cDNA amplification, detection and sequencing are typically DNA based oligonucleotides. However, the second oligonucleotide according to the present invention further comprises up to 10 non-DNA based nucleotide residues, i.e. 1 to 5 isomeric nucleotide residues as a blocking sequence, and optionally 1 to 5 ribo-G nucleotide residues complementary to the C nucleotide residues incorporated in the first cDNA strand. Of note, the "second molecule" herein is not identical to the "second oligonucleotide". Rather "second molecule" is the first oligonucleotide that is eventually elongated to the full first cDNA strand.

In some embodiments, optionally a second identifier sequence of 6 to 12, preferably 10, nucleotide residues in length is comprised in said second oligonucleotide. In particular, said second identifier sequence is flanked by the second primer recognition sequence at one end and by the ribo-G nucleotide residues in case they are comprised in the second oligonucleotide sequence.

As regards the second primer recognition sequence and the second identifier sequence the same applies as described above in connection with the first primer recognition sequence and the first identifier sequence. The first identifier sequence and the second identifier sequence can have the same nucleotide sequence, partially the same nucleotide sequence or different nucleotide sequences.

Elongation of the cDNA Strand, Part II

According to the present invention, upon contacting the sample under study with a plurality of said second oligonucleotides the 3' end of a first cDNA strand is enzymatically elongated, wherein a second oligonucleotide serves as the template.

In other words, a generated first cDNA strand comprises in 5' to 3' direction i) said first oligonucleotide, ii) a sequence complementary to a polyribonucleotide except nucleotides comprised already in the 3' end of said first oligonucleotide and thus enabled hybridization between the first oligonucleotide and said polyribonucleotide, iii) 1 to 5 nucleotide residues, preferably 1 to 5 C nucleotide residues, more preferably 3 C nucleotides, iv) a sequence complementary to said second oligonucleotide except the part consisting of a blocking sequence, preferably consisting of isomeric nucleotide residues and except the part consisting of ribo-G nucleotide residues in case said oligonucleotide comprises ribo-G nucleotide residues.

cDNA Library Generation Using PCR

According to the present invention, as a next step, the second strand of cDNA is generated and the double-stranded cDNA is amplified to generate the cDNA library using a nucleic acid amplification reaction, preferably PCR.

In other words, the step of obtaining an extended second molecule is followed by amplifying said obtained extended second molecule, preferably by PCR.

It can also be said that a cDNA library is generated, preferably using PCR, based on the polyribonucleotides comprised in a sample under study.

Hence, generated first cDNA strands are separated from the second oligonucleotides and the polyribonucleotides. Next, a primer pair is brought in contact with the generated single-strand first cDNA strand. Said primer pair consists of two primers, wherein the first primer has a sequence that is complementary to the first primer recognition sequence and the second primer has a sequence corresponding to the second primer recognition sequence comprised in the generated first cDNA strand, or wherein the first primer has a sequence corresponding to the first primer recognition sequence and the second primer has a sequence complementary to the second primer recognition sequence comprised in the generated first cDNA strand, respectively. Upon hybridization of the primer having a complementary sequence to one of the two primer recognition sequences comprised in the first cDNA strand, the second cDNA strand is synthesized. The two cDNA strands are separated again and each is used as a template for the synthesis of a complementary strand using one of the two primers of the respective primer pair that can hybridize to the respective cDNA strand.

For PCR based amplification of generated first cDNA strands the steps of strand separation, primer hybridization and second cDNA strand synthesis are performed iteratively as it is known to the person skilled in the art.

Alternatively, instead of PCR, for example Recombinase Polymerase Amplification (RPA) can be performed.

Hence, by applying the method according to the present invention entire polyribonucleotide sequences are obtained transcriptome-wide, preferably entire sequences of lncRNA molecules and/or isoforms of mRNA molecules present in a sample. In particular, the method as described above enables sequencing of cDNA molecules comprising the entire sequence of a given mRNA isoform and its respective poly(A) tail with high accuracy.

According to the present invention, the step of obtaining an extended second molecule is preferably performed using a Moloney murine leukemia virus (MMLV) reverse transcriptase and/or an enzyme having the same function as said MMLV reverse transcriptase, wherein said function comprises reverse transcription, terminal nucleotidyl-transferase and template switching.

A MMLV reverse transcriptase is an RNA-dependent DNA polymerase that can use RNA, DNA, or an RNA-DNA hybrid to synthesize complementary DNA strands. MMLV reverse transcriptases are commercially available and known to the person skilled in the art. In particular, an MMLV reverse transcriptase can switch template from a single-stranded RNA molecule to a second oligonucleotide during first cDNA strand synthesis. Template switching is enabled by the terminal nucleotidyl-transferase activity that enables the MMLV reverse transcriptase to add nucleotide residues to the end of a polyribonucleotide upon reaching the terminus of said polyribonucleotide during first cDNA strand synthesis, i.e. reverse transcription of the polyribonucleotide. The second oligonucleotide can transiently anneal to the added nucleotide residues by virtue of a complementary nucleotide sequence. The enzyme then switches template from the polyribonucleotide to the second oligonucleotide and continues with first cDNA strand synthesis. Hence, additional nucleotide sequences such as primer recognition sequences or identifier sequences can be efficiently incorporated into a first cDNA strand. The use of an MMLV reverse transcriptase is advantageous for the preparation of cDNA libraries and first strand cDNA synthesis for use in PCR reactions.

In some embodiments, an MMLV reverse transcriptase adds 1 to 5 C nucleotide residues to the 3' end of the first cDNA strand, i.e. the end of the first cDNA strand that is not complementary to the poly(A) tail of the mRNA molecule in case the polyribonucleotide is an mRNA molecule.

In particularly preferred embodiments, an MMLV reverse transcriptase adds 3 C nucleotide residues to the 3' end of the first cDNA strand.

In some embodiments, an enzyme other than an MMLV reverse transcriptase is used to add 1 to 5 C nucleotide residues to the 3' end of the first cDNA strand, wherein said enzyme has the same function as an MMLV reverse transcriptase, wherein said function comprises reverse transcription, terminal nucleotidyl-transferase and template switching.

Depending on the enzyme to be used other nucleotides than C nucleotides can be added and used for template switching. In this case, the second oligonucleotide preferably comprises 1 to 5, more preferably 3, ribonucleotides complementary to said added nucleotides other than C nucleotides.

According to the present invention, the method for analyzing a polyribonucleotide preferably can further comprise the step of obtaining data for said extended second molecule, preferably using a sequencing method, more preferably a Third Generation sequencing method. Thus, preferably a long read sequencing technology is used.

In other words, the generation of a cDNA library from a sample comprising a plurality of polyribonucleotides is preferably followed by sequencing the members of said cDNA library using a Third Generation sequencing method, preferably a sequencing method selected from the group consisting of PacBio® Single Molecule, Real-Time (SMRT®) sequencing or Oxford Nanopore Technologies® nanopore DNA sequencing, thereby obtaining the sequence of said polyribonucleotides in said sample.

Several Third Generation sequencing technologies are commercially available so far and can be mainly associated to one of three categories: (i) technologies that are based on observing the synthesis of a DNA molecule by a DNA polymerase; (ii) nanopore-sequencing technologies that are based on threading DNA through a nanopore and detecting nucleotides when passing through such a nanopore; and (iii) technologies that are based direct imaging of DNA molecules using advanced microscopy techniques. As these technologies have different advantages and disadvantages, a suitable technology may be chosen according to the respective experimental setting and research question. Platforms and respective technologies are available for example by Epicentre™, Clontech®, and Lexogen®, preferably by Pacific Biosciences® and Oxford Nanopore Technologies®.

However, current Third Generation Sequencing protocols are not optimized for simultaneously analyzing the entire sequences of mRNA isoforms in conjunction with their respective poly(A) tail transcriptome-wide. The method according to the present invention allows obtaining sequencing data, preferably long-read sequencing data, that comprise information of the complete cDNA and thus, of the entire original polyribonucleotide sequence. This is particularly advantageous in case of complex genomes and transcriptomes as for example in case of plant genomes and transcriptomes.

Obtained data are preferably checked for quality aspects and optionally filtered for quality criteria known to persons skilled in the art. Data can be grouped according to samples they originated from based on the investigation of identifier sequences comprised in the obtained extended second molecules and/or the obtained cDNA molecules used for sequencing. Preferably, said molecules are labeled at single-cell resolution. Thus, exact information regarding polyribonucleotide sequence and length can be obtained on a single-cell level and/or sample level. In particular, in case of polyribonucleotides being mRNA molecules comprehensive information regarding mRNA and poly(A) tail sequence and length can be jointly obtained with high accuracy and sensitivity in high-throughput. This includes for example also information on different mRNA isoforms and/or mRNA molecules that were subjected to varying splicing processes as well as UTR isoforms and/or quantitative information based for example on the amount of sequencing reads obtained for a given polyribonucleotide.

According to the present invention, the method can further comprise the step of comparing results for said polyribonucleotide to results obtained by a method according to the present invention for at least another polyribonucleotide and/or to information obtained by other methods at least for said polyribonucleotide.

In other words, obtained sequencing data can be compared to available data such as, but not limited to reference genome and/or transcriptome data, preferably annotated reference genome and/or transcriptome data. Data can also be compared to available expression values and/or information of copy number variations and/or presence/absence variations and/or information on the presence of mutations.

According to the present invention, wherein at least one of the steps described above, preferably all steps, is followed by a purification step, preferably using magnetic beads. In particular, at least one of the steps a) obtaining a labeled polyribonucleotide, b) providing a second molecule, c) obtaining a complex of said labeled polyribonucleotide and said second molecule, and d) obtaining an extended second molecule is followed by a purification step, preferably using magnetic beads.

Purification can be done by several methods known to the person skilled in the art such as, without being limited to centrifugation, chloroform extraction, and/or ethanol precipitation. Magnetic bead based purification methods comprise binding, washing, and elution steps. The basic principle of such methods is the use of magnetic beads functionalized with silica surfaces that allow selective binding of RNA, DNA, and/or cDNA molecules, preferably in the presence of high concentrations of salt. Bound molecules can be easily separated from other reagents and/or molecules using a magnet. Hence, magnetic bead based purification methods are advantageous for rapid sample processing and automated high-throughput analyses. The exemplarily use of Ampure xp beads that use electrostatic binding to molecules comprising nucleotides is for example shown in the appended examples.

According to the present invention, a method for generating a cDNA library from a sample comprising a plurality of polyribonucleotides comprises the steps of: (a) enzymatically elongating the 3' end of the polyribonucleotides with a random sequence of 1 to 20, preferably 1 to 5, G and I nucleotide residues, (b) contacting said sample with (b1) a plurality of first oligonucleotides comprising in 3' to 5' direction (i) 0 to 12, preferably 1 to 7 T nucleotide residues, (ii) 5 to 15, preferably 8 to 10 C nucleotide residues, (iii) optionally a first identifier sequence of 6 to 12, preferably 10, random nucleotide residues in length, and (iv) a first primer recognition sequence of 18 to 35 nucleotide residues in length, so as to allow hybridization of said first oligonucleotides to said polyribonucleotides, and (b2) a plurality of second oligonucleotides comprising in 5' to 3' direction (i) a blocking sequence, preferably consisting of 1 to 5 isomeric nucleotide residues, more preferably of 3 isomeric C nucleotide residues or of 1 isomeric G nucleotide residue flanked by 2 isomeric C nucleotide residues, (ii) a second primer recognition sequence of 18 to 35 nucleotide residues in length, and (iii) optionally 1 to 5 ribo-G nucleotide residues complementary to the C nucleotide residues incorporated in the first cDNA strand, so as to allow hybridization of said second oligonucleotides to said first cDNA strands, (c) enzymatically elongating said hybridized first oligonucleotides using a reverse transcriptase enzyme, wherein said polyribonucleotides serve as the template, thereby generating the first strand of cDNA, (d) enzymatically elongating the 3' end of said first cDNA strand with 1 to 5 nucleotide residues, preferably 1 to 5 C nucleotide residues, so as to allow hybridization of said second oligonucleotides to said polyribonucleotides in said sample, (e) enzymatically elongating the 3' end of said first cDNA strand, wherein said second oligonucleotide serves as the template, and (f) generating the second strand of cDNA and amplifying the double-stranded cDNA to generate the cDNA library using a nucleic acid amplification reaction, preferably PCR.

As regards the generation of the cDNA library the same applies as described above in connection with the method of analyzing a polyribonucleotide. Moreover, also the other features of such a method can be as described above.

According to the present invention, the method of sequencing a plurality of polyribonucleotides in a sample comprises (a) generating a cDNA library as described above, and (b) sequencing the members of said cDNA library using a Third Generation sequencing method, preferably a sequencing method selected from the group consisting of PacBio® SMRT® sequencing or Oxford Nanopore Technologies® nanopore DNA sequencing, thereby obtaining the sequence of said polyribonucleotides in said sample.

As regards the generation of the cDNA library and the sequencing of the cDNA library members the same applies as described above in connection with the method of analyzing a polyribonucleotide and sequencing the respective extended second molecule. Moreover, also the other features of such a method can be as described above.

Figure 1:
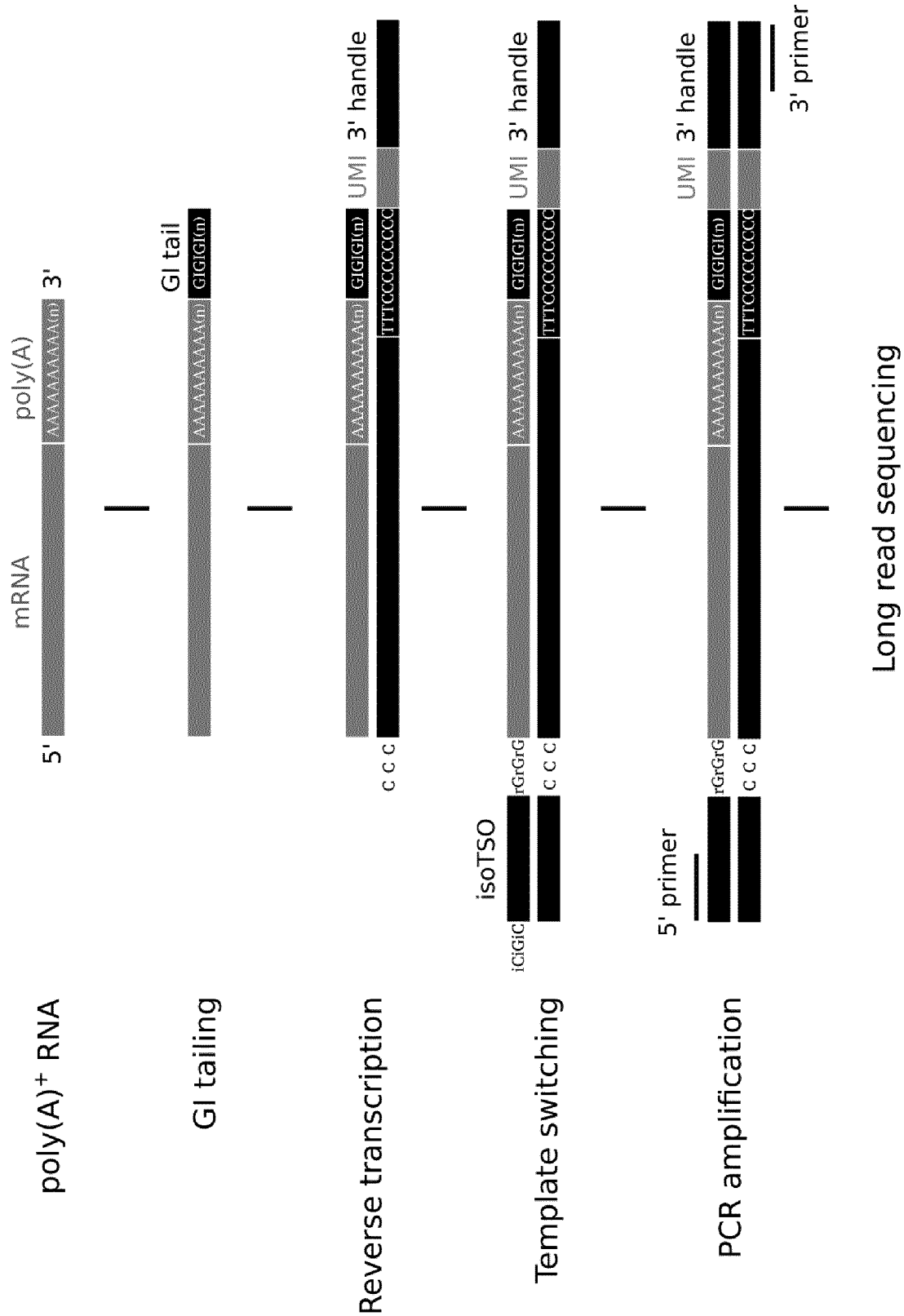
FIG. 1: Scheme of the library preparation method.
Figure 2:
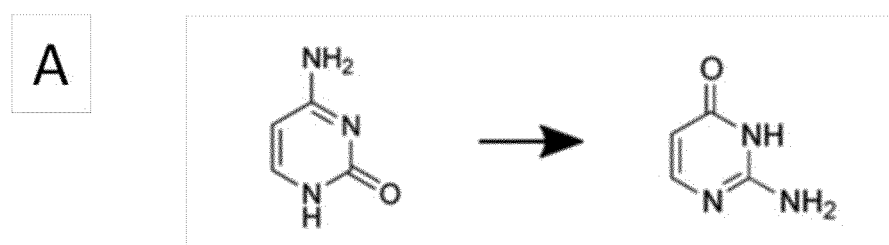
FIG. 2: Isomers of the nitrogenous bases cytosin (A) and guanine (B) with the isomer naturally occurring in nucleotides being depicted on the left side and the respective isomers preferably used herein depicted on the right side.
Figure 2:
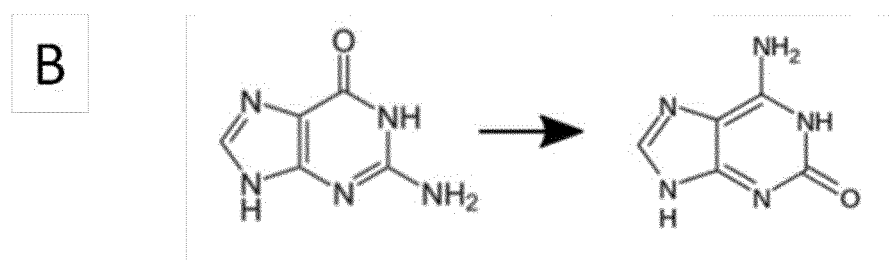

Other aspects and advantages of the invention will be described in the following examples, which are given for purposes of illustration and not by way of limitation. Each publication, patent, patent application or other document cited in this application is hereby incorporated by reference in its entirety.

EXAMPLES

Methods and materials are described herein for use in the present disclosure; other, suitable methods and materials known in the art can also be used. The materials, methods, and examples are illustrative only and not intended to be limiting.

Material and Methods

RNA Input
  Any synthetic RNA or RNA derived from a biological sample can be used for analysis.
Poly(A)+ Purification
  Total RNA (10 µg)
  1:100 ERCC spike ins (Mix 1, cat: 4456740, Thermo Fisher)
  Total volume 50 µl
  Use Illumina Truseq mRNA preparation kit (cat. RS-122-2102 Illumina) or any equivalent oligo dT-based method for mRNA purification.
  Vortex RNA purification beads (RNAClean XP Beads, cat. A63987, Beckmann Coulter) in a tube and add 50 µl to the obtained purified RNA sample.
  Pipet the mixture up and down 6 times to mix.
  Incubate the mixture in a thermocycler at 65° C. for 5 minutes (min), put it on ice for 5 min and perform reverse transcription (RT) for 5 min.
  Place the mixture in a rack and the rack into a magnetic separator for 5 min.
  Remove and discard the supernatant.
  Remove the mixture from the rack and transfer it into a new tube.
  Add 200 µl of Bead Washing Buffer and pipet up and down 6 times to mix the Bead Washing Buffer and the mixture comprising the RNA sample.
  Place the tube comprising the RNA sample back into the magnetic separator for 5 min.
  Remove and discard the supernatant.
  Add 50 µl of Elution Buffer and pipet up and down 6 times.
  Incubate the mixture in a thermocycler at 80° C. for 2 min.
  Remove the mixture from the thermocycler and keep it at room temperature for 5 min.
  Add 50 µl of Bead Binding Buffer and pipet up and down 6 times.
  Incubate the mixture at room temperature for 5 min.
  Place tube containing the mixture comprising the RNA sample in the rack and the rack into the magnetic separator for 5 min.
  Remove and discard the supernatant.
  Remove the mixture comprising the RNA sample from the rack and transfer it into a new tube.
  Add 200 µl of Bead Washing Buffer and pipet up and down 6 times.
  Place the tube containing the mixture comprising the RNA sample back into the magnetic separator for 5 min.
  Remove and discard all supernatant.
  Add 16 µl dH$_2$O/10 mm Tris HCl pH 7.5 and pipet up and down 6 times.
  Incubate mixture in the thermocycler at 70° C. for 2 min and put it on ice for 1 min.
  Place the tube comprising the RNA sample in a magnetic rack for 5 min.
  Transfer 16 µl of the supernatant to a new 0.2 ml PCR tube.
  Keep 1 µl of the supernatant for an analysis using a Bioanalyzer pico chip.
Ribodepletion
  Alternatively or additionally to poly(A)+ purification, lncRNA molecules and/or mRNA molecules having a poly(A) tail can be enriched by ribodepletion, i.e. by removing ribosomal RNA (rRNA) from total RNA.
  Ribodepletion can be performed as described in Adiconis et al., 2013, Nat Methods, 10(7):623-9. In particular, ribodepletion can be performed as follows:
Materials
  1) 5× Hybridization buffer: 1 M NaCl, 0.5 M Tris-HCl pH 7.5
  2) 5× RNase H buffer: 1 M NaCl, 0.5 M Tris-HCl pH 7.5, 250 mM MgCl$_2$
  3) rRNA DNA oligos: concentration 2.5 µg/µL oligos use 1:2 (by mass) on total RNA (e.g. 1 µg oligos for 500 ng total RNA)
  4) Hybridase thermostable RNase H (Epicentre, 5 U/µL)
  5) RNA Cleanup XP beads (Agencourt)
  6) 80% EtOH
  7) Turbo DNase Treatment & Removal Kit (Ambion)
  Oligos: designed as a tiling oligo mix similar to Adiconis et al., 2013, Nat Methods, 10(7):623-9, for species of choice against all annotated rRNAs
  5 µg total RNA
  20 µg DNA oligos (8 µl)
  5 µl ERCC spike ins 1:100
  6 µl 1× hybridization buffer
  final volume 30 µl Ribodepletion Heat at 95° C. for 2 min, cool to 45° C. slowly (0.1° C./s) in thermoblock Add 20 µl of 45° C. pre-warmed RNase H mix:

10 µl Hybridase (5 U/µL)

10 µl 5× RNase H buffer

Incubate for 30 min at 45° C., put on ice

Extract RNA with RNA Cleanup XP beads from Agencourt XP, add 0.6×volume beads per sample (30 µl), mix well by pipetting, incubate for 5 min, put on magnet for 5 min, remove supernatant and wash twice for 30 s with 80% EtOH, let beads dry at room temperature for 10 min, resuspend in 25 µl $H_2O$ Add 3 µL DNase buffer (10×), 2 µL DNase (2 U/µl, i.e. 'rigorous treatment') Incubate at 37° C. for 30 min, add 5 µl inactivation reagent, incubate for 2 min at room temperature Purify RNA again with RNA Cleanup XP beads as described above Elute in 16 µl $H_2O$ G/I Tailing Using USB polyA Length Assay Kit (Cat. 764551KT, ThermoFisher)

| Reagent | Per reaction |
|---|---|
| poly(A)+ RNA | 14 µl |
| 5X tail buffer mix | 4 µl |
| 10X tail enzyme mix | 2 µl |
| Total volume | 20 µl |

Incubate the mixture at 37° C. for 60 min.

Add 1.5 µl tail stop solution to the mixture and keep it on ice.

Keep 1 µl of the iced mixture for an analysis using a Bioanalyzer pico chip.

GI Tailed RNA Purification

Add 1.8×XP RNA beads to the iced mixture and incubate it at room temperature for 5 min.

Put it in a magnetic rack, and keep it for 3 min.

Remove the supernatant.

Wash twice with 50 µl ethanol 80% for 30 seconds.

Remove the supernatant, and leave tubes open for 10 min.

Resuspend the beads in 18 µl $dH_2O$

Keep 1 µl of the resuspended beads for an analysis using a Bioanalyzer pico chip.

Reverse Transcription (Using SMARTScribe Reverse Transcriptase Kit, Cat. 639537, Clontech)

| Prepare a | 22 µl mastermix |
|---|---|
| 5X First strand buffer | 8 µl |
| DTT 20 mM | 1.5 µl |
| dNTP mix 10 mM | 4 µl |
| RNase Inhibitor | 2 µl |
| isoTSO 12 µM | 2 µl |
| SMARTScribe RT 100 u | 2 µl |
| $dH_2O$ | 2.5 µl |
| Total volume | 22 µl |

Prepare the mastermix by mixing the reagents and keep the mastermix at room temperature.

| Reagent | RT |
|---|---|
| G/I Tailed RNA Sample | 16 µl |
| dC 3T UMI RT primer10 µM | 2 µl |

Mix contents in a tube and spin the tube briefly. Put it in the thermocycler and start the following program:

Incubate the mastermix at 72° C. for 3 min, at 42° C. for 60 min, wherein after the first 2 min the RT mix are added, at 70° C. for 10 min, and hold them at 4° C.

cDNA Purification

Add 0.6×XP DNA beads to the mixture obtained upon RT and incubate at room temperature for 5 min.

Put the mixture in a magnetic rack and keep it for 3 min.

Remove the supernatant.

Wash twice with 50 µl ethanol 80% for 30 seconds.

Remove the supernatant, and leave tubes open for 10 min.

Resuspend the beads in 42 µl $dH_2O$.

Keep 1 µl for an analysis using a Bioanalyzer picochip.

PCR Amplification (Using Advantage 2 PCR Enzyme System)

| Reagent | Volume |
|---|---|
| 10X Advantage 2SA PCR buffer | 10 µL |
| Diluted first-strand cDNA from step above | 40 µL |
| dNTP Mix (10 mM each) | 2 µL |
| 5' PCR Primer II A (12 µM) | 2 µL |
| Univ. RV Primer (10 µM) | 2 µl |
| Nuclease-free water | 42 µl |
| 50X Advantage 2 Polymerase Mix | 2 µL |
| Total Volume | 100 µL |

Put the reagents into a thermocycler, which already reached 98° C. and start the following program: 98° C. for 1 min; 23 cycles: 98° C. for 10 seconds, 63° C. for 15 seconds, and 68° C. for 3 min; 68° C. for 3 min.

23 cycles was found to be a good number of cycles for starting with 10 µg of HeLa S3 RNA. If the type of RNA sample has never been processed before, PCR optimization is recommended by splitting the 100 reaction into 4 tubes with 25 µL each and test 18, 20, 22, and 24 cycles.

Check the PCR product on a 1.5% agarose gel and with a fragment analyzer.

Continue if the library is good (typically smooth profile peaking at 1.5 kb).

Library Purification

Add 0.6×XP DNA beads (cat. A63881, Beckmann Coulter), incubate at RT for 5 min.

Put on magnetic rack, keep for 3 min.

Remove supernatant.

Wash twice with 50 µl Ethanol 80% for 30 seconds.

Carefully remove supernatant, leave tubes open for 10 min.

Resuspend beads in 42 µl dH$_2$O, put on rack 3 min, recover supernatant.

Proceed with preferred sequencing method.

Oligonucleotide Sequences

```
isoTSO
iCiGiCAAGCAGTGGTATCAACGCAGAGTGGCCATTACGGCCrGrGrG dC 3T RT UMI primer
GGTAATACGACTCACTATAGCGAGANNNNNNNNNNNCCCCCCCCCTTT alternative RT primer
TGAGTCGGCAGAGAACTGGCGAANNNNNNNNNNNCCCCCCCCCTTT PCR primer reverse
GGTAATACGACTCACTATAGCGAG alternative PCR primer reverse
TGAGTCGGCAGAGAACTGGCGAA
``` with
- i: isomeric
- r: ribonucleotide
- A, C, G, and T: nucleotide having an adenine, cytosine, guanine, and thymine as nitrogenous base, respectively
- N: nucleotide having any nitrogenous base Computational Analysis A computational analysis pipeline was implemented as Bash script comprising several Python scripts and additional tools for performing different analysis steps.

The pipeline makes use of STARLong (github.com/alexdobin/ST AR/blob/master/bin/Linux_x86_64/STARlong) that is available under GPLv3 license.

The pipeline also makes use of the Subread FeatureCounts software (subread.sourceforge.net/).

Sequencing Raw Data are converted to standard FASTQ Format using sequencing device supplied software (e.g. PacBio® SMRT® Link). In order to recover poly (A) tail length measurements for individual sequenced molecules, reads as processed as follows:

1)
  a) Reads are examined for characteristic CCC(n)TTT(m) nucleotide stretches within the first 100 nucleotides (nt) from read start, e.g. the start of a read as stored in a fastq file, wherein n and m refer to two integers.
  b) Reads are examined for characteristic AAA(m)GGG(m) nucleotide stretches within the last 100 nt. Reverse complements are computed for b) reads, such that they align with reads from a).
  c) Other reads are discarded, i.e. reads not comprising a CCC(n)TTT(m) or a AAA(m)GGG(m) nucleotide stretch.

2) For identification of each read's putative poly(A) tail sequence, reads are analyzed by two algorithms each comprising a different parameter combination. Finally, the reported poly(A) tail length and sequence are assigned by a majority vote between the results produced by each run of each algorithm. 4 runs are performed with Algorithm 1 and 6 runs with Algorithm 2. The tail length that is more frequently reported by the algorithms is considered to be the measured length.
  a) Algorithm 1: Extended Mismatch approach:
    Each read's sequence is searched from the beginning for 10 subsequent T's with a maximum of one mismatch. This seed sequence is extended by searching for adjacent T's until the number of mismatches observed in the gathered 'poly(A) tail' sequence is higher than a given threshold number for (number gathered T's/threshold) in relation to a given gathered sequence. In this case, the end of the poly(A) tail is reported at this position. The threshold parameter can be varied by the user.
  b) Algorithm 2: Sliding Window:
    A sliding window of length n is run across the read sequence. If the fraction of T nucleotides per sliding window drops below a threshold, this position is defined as the end of the tail.
  c) Majority vote:
    Typically, four runs of Algorithm 1 are performed with threshold values of 25, 30, 35 and 40. Six runs of Algorithm 2 are performed by combining the values 20, 25 and 30 for the sliding window and 80% and 85% for the threshold. The tail length reported most of the times is taken as the actual tail length.
    Poly(A) tail length and inferred sequence are reported for each read and the respective reads are removed from the raw sequence.

3) The remaining fraction of reads is aligned to the reference genome of the species the samples are collected from using STARLong. The alignments are then assigned to individual genes using FeatureCounts. Read length for individual genes are aggregated using custom Python scripts.

4) UTR Isoforms are annotated by extracting the corresponding positions for the sequenced molecule 3' end from the aligned reads. Python findpeaks is used to identify peaks in putative UTR end. Peaks are aggregated to UTR isoforms and alignments are sorted by each UTR isoform. UTR specific aggregated data comprising isoform counts, isoform poly (A) tail length and other features are reported as matrix for analysis using statistics software e.g. R Studio.

5) UTR Isoforms are annotated by inspecting the first splice site of reads in each UTR group and comparing to exon annotations for the genome of choice, e.g. Gencode). UTR annotations are again aggregated and reported as matrix file.

Exploratory Application

Sequencing a cDNA library generated from polyribonucleotides such as lncRNA molecules and/or full-length mRNAs with poly(A) tails according to the present invention allows identifying the entire polyribonucleotide sequence including the full-length poly(A) tail in case of mRNA molecules. Moreover, it allows to associate features of the poly(A) tail with any other feature comprised in the respective mRNA sequence, i.e. the respective transcript sequence, such as, without being limited to, UTRs and splicing patterns.

HeLa S3 Cells-Derived mRNA was Used for Exploring this Possibility.

Figure 3:
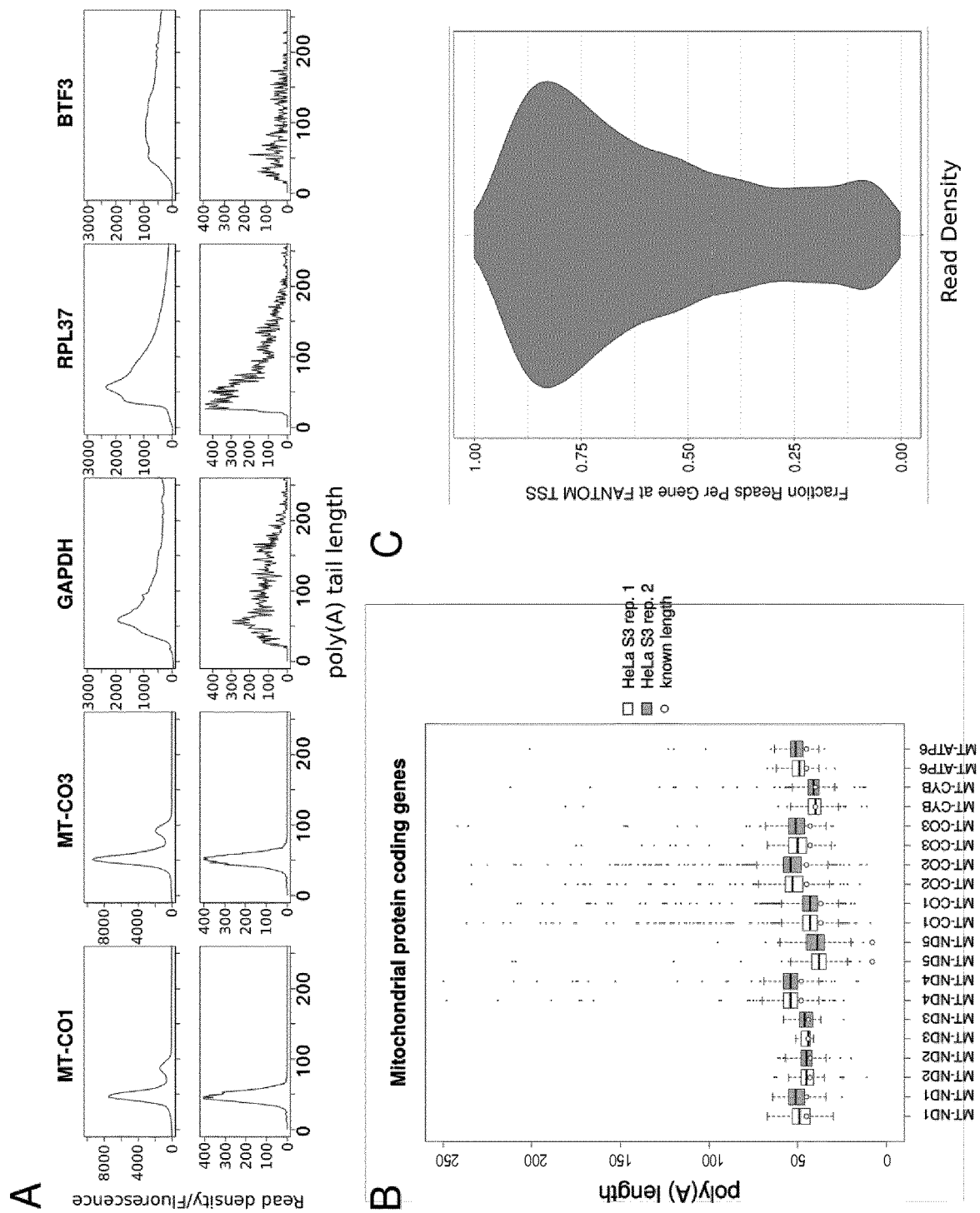
FIG. 3: A. Validation of poly(A) tail length of 5 genes from HeLa S3 cells, by HirePAT assay (up) compared with sequencing data (down). B. measured poly(A) tail length distribution for mitochondrial protein coding genes in two HeLa S3 cells RNA replicates (in white and grey boxes, medians as black solid lines), compared to typical poly(A) tail length of the same mRNAs (white dots) measured in Temperley et al., 2010 (Temperley et al., 2010, Biochim Biophys Acta., 1797(6-7):1081-5). C. Distribution of fraction of reads from HeLa S3 cells RNA spanning the FANTOM annotated transcription start sites.

In FIG. 3A the length of poly(A) tails of mRNAs originating from 5 genes was estimated by Hire-PAT assay (upper panels). The result compared very well with the poly(A) tail length distribution that resulted from full-length RNA sequencing according to the present invention (lower panels). An additional control of the accuracy of the method came from mitochondrial mRNAs, which have well defined poly(A) tail lengths that were measured using other approaches (Temperley et al., 2010).

In FIG. 3B, white and dark grey boxplots show the distribution of poly(A) tail lengths for all mitochondrial mRNAs in two replicates of HeLa cells, while white dots represent previously published poly(A) tail lengths. Only for one gene, MT-ND5, the method according to the present invention resulted in a larger poly(A) tail estimate. This is not actually a mistake but corresponds to a population of this mRNAs having a longer tail (Temperley et al., 2010), while the mRNAs with very short tail are discarded by the analysis pipeline.

In FIG. 3C is shown that a high proportion of the generated reads contain or overlap with transcription start sites (TSS) annotated by the FANTOM5 project, showing that the reads usually span whole transcripts.

A second major advance of the method according to the present invention relates to the capacity of capturing full length mRNAs, in particular isoform variants together with their respective poly(A) tail length and composition. This is particularly advantageous for investigating and/or comparing one or more mRNAs and/or mRNA isoforms of interest and/or for analyzing the entire sequences of mRNA isoforms in conjunction with their respective poly(A) tail transcriptome-wide.

Figure 4:
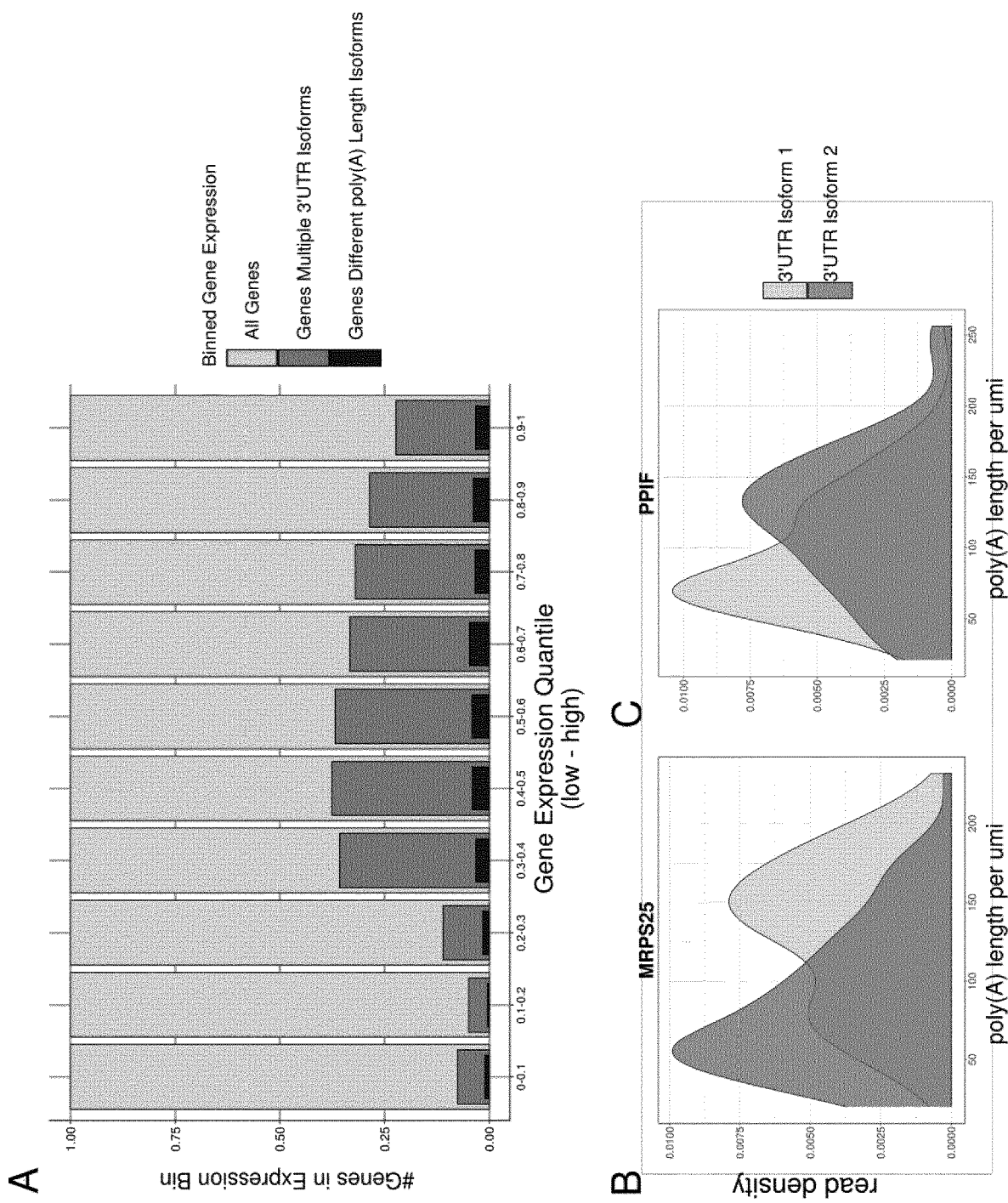
FIG. 4: A. Fraction of all genes (light grey) with multiple UTR isoforms (grey) and with different poly(A) tail length associated with different isoforms (black), per quantile of gene expression, from HeLa S3 cells RNA. B and C. Two examples of two genes with different UTR isoforms (light and dark grey) that have different poly(A) tail distributions.

Applying the method according to the present invention allowed to show that thousands of genes produce multiple 3' UTR isoforms with hundreds of them having different poly(A) tail lengths (FIG. 4A, proportion of genes, genes with multiple 3' UTRs and genes with significantly different poly(A) tails for different UTRs are reported by expression level quantile).

Two examples, namely MRPS25 and PPIF, are shown in FIGS. 4B and C.

Figure 5:
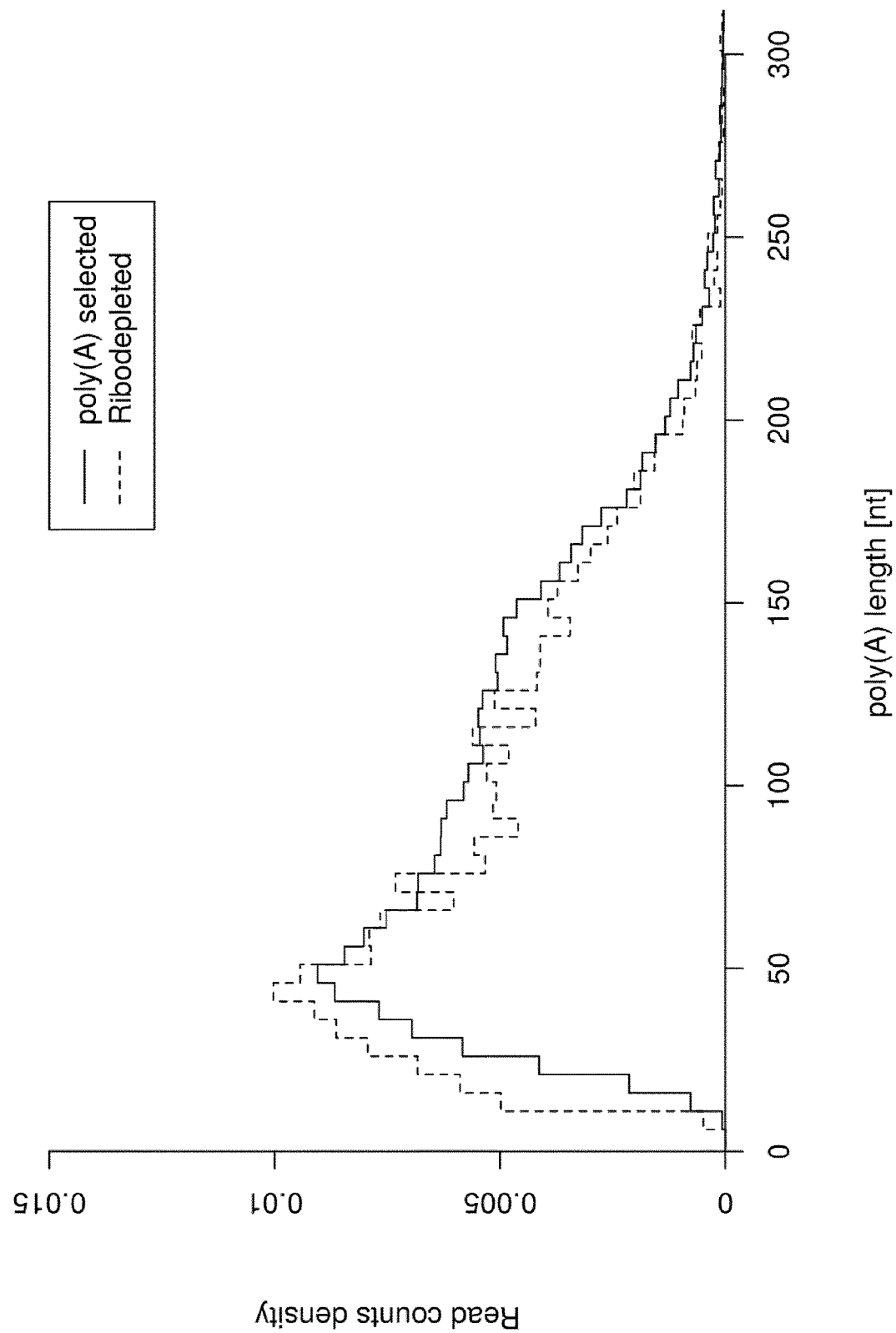
FIG. 5: Poly(A) tail distribution after enriching lncRNA molecules and/or mRNA molecules with a poly(A) tail in HeLa S3 cell RNA by poly(A)+ purification (solid line) and ribodepletion (dashed line), respectively.

In FIG. 5 is exemplarily shown the poly(A) tail distribution obtained from HeLa S3 cell RNA after poly(A)+ tail purification and ribodepletion, respectively. Both methods can thus be used alternatively or additionally for enriching lncRNA molecules and/or mRNA molecules having a poly(A) tail from total RNA.

The invention claimed is:

1. A method for analyzing a polyribonucleotide, said method comprising the following steps:
   (a) obtaining a labeled polyribonucleotide by linking the 3' end of said polyribonucleotide and a random sequence of 1 to 20 G and I nucleotide residues; followed by
   (b) providing a second molecule comprising:
   (b1) a first primer recognition sequence of 18 to 35 nucleotide residues in length that defines the 5' end of said second molecule, followed by
   (b2) a sequence of 5 to 15 C nucleotide residues linked to a sequence of 0 to 12 T nucleotide residues which define the 3' end of said second molecule;
   followed by
   (c) obtaining a complex of said labeled polyribonucleotide and said second molecule comprising a double-stranded sequence consisting of sequence (b2) of the second molecule and the complementary 3' end sequence of the labeled polyribonucleotide; followed by
   (d) obtaining an extended second molecule by
   (d1) extending the 3' end of the second molecule comprised in the complex obtained from step (c) by synthesizing a sequence that is complementary to the part of the sequence of the labeled polyribonucleotide which is not part of the double-stranded sequence comprised in the complex; followed by
   (d2) extending the 3' end of the second molecule obtained from step (d1) by adding at least (i) 1 to 5 C nucleotide residues, followed by (ii) a second primer recognition sequence of 18 to 35 nucleotide residues in length,
   wherein the polyribonucleotide is an mRNA molecule with a poly(A) tail,
   said method further comprising obtaining data for said extended second molecule using a Third Generation sequencing method.

2. The method according to claim 1, wherein step (d) is performed using a Moloney murine leukemia virus (MMLV) reverse transcriptase and/or an enzyme having the same function as said MMLV reverse transcriptase, wherein said function comprises reverse transcription, terminal nucleotidyl-transferase and template switching.

3. The method according to claim 1, wherein step (d) is followed by amplifying said obtained extended second molecule (step (e)).

4. The method according to claim 1, wherein the method further comprises comparing results obtained by said method for said polyribonucleotide to results obtained for at least another polyribonucleotide and/or information obtained by other methods at least for said polyribonucleotide.

5. The method according to claim 1, wherein at least one of the steps is followed by a purification step.

6. The method according to claim 1, the second molecule comprising:
   (b1) a first primer recognition sequence of 18 to 35 nucleotide residues in length that defines the 5' end of said second molecule, followed by
   (b2) a sequence of 8 to 10 C nucleotide residues linked to a sequence of 1 to 7 T nucleotide residues which define the 3' end of said second molecule.

7. A method for generating a cDNA library from a sample comprising a plurality of polyribonucleotides, the method comprising the steps of:
   (a) enzymatically elongating the 3' end of the polyribonucleotides with a random sequence of 1 to 20 G and I nucleotide residues,
   (b) contacting said sample with:
   (b1) a plurality of first oligonucleotides comprising in 3' to 5' direction:
   (i) 0 to 12 T nucleotide residues,
   (ii) 5 to 15 C nucleotide residues,
   (iii) optionally a first identifier sequence of 6 to 12 random nucleotide residues in length, and
   (iv) a first primer recognition sequence of 18 to 35 nucleotide residues in length, so as to allow hybridization of said first oligonucleotides to said polyribonucleotides,
   and
   (b2) a plurality of second oligonucleotides comprising in 5' to 3' direction;
   (i) a blocking sequence of 1 to 5 isomeric nucleotide residues, 3 isomeric C nucleotide residues or of 1 isomeric G nucleotide residue flanked by 2 isomeric C nucleotide residues,
   (ii) a second primer recognition sequence of 18 to 35 nucleotide residues in length, and
   (iii) optionally 1 to 5 ribo-G nucleotide residues complementary to the C nucleotide residues incorporated in a first cDNA strand,
   so as to allow hybridization of said second oligonucleotides to said first cDNA strands,
   (c) enzymatically elongating said hybridized first oligonucleotides using a reverse transcriptase enzyme, wherein said polyribonucleotides serve as the template, thereby generating the first strand of cDNA,
   (d) enzymatically elongating the 3' end of said first cDNA strand with 1 to 5 nucleotide residues, so as to allow hybridization of said second oligonucleotides to said polyribonucleotides in said sample,
   (e) enzymatically elongating the 3' end of said first cDNA strand, wherein said second oligonucleotide serves as the template, and
   (f) generating a second strand of cDNA and amplifying the double-stranded cDNA to generate the cDNA library using a nucleic acid amplification reaction, wherein said polyribonucleotides are mRNA molecules with a poly (A) tail, and wherein said method further comprises sequencing the members of said cDNA library using a Third Generation sequencing method.

8. The method according to claim 7, the plurality of first oligonucleotides comprising in 3' to 5' direction:
  (i) 1 to 7 T nucleotide residues,
  (ii) 8 to 10 C nucleotide residues,
  (iii) optionally a first identifier sequence of 6 to 12 random nucleotide residues in length, and
  (iv) a first primer recognition sequence of 18 to 35 nucleotide residues in length.

9. A method of sequencing a plurality of polyribonucleotides in a sample, the method comprising
  (a) generating a cDNA library using the method according to claim 7, and
  (b) sequencing the members of said cDNA library using a sequencing method selected from the group consisting of Single Molecule, Real-Time DNA sequencing and nanopore DNA sequencing, thereby obtaining the sequence of said polyribonucleotides in said sample.

* * * * *